(12) United States Patent
Wang et al.

(10) Patent No.: US 10,195,176 B2
(45) Date of Patent: Feb. 5, 2019

(54) METHODS AND COMPOSITIONS FOR INHIBITION OF ATR AND FANCD2 ACTIVATION

(71) Applicant: Kaohsiung Medical University, Kaohsiung (TW)

(72) Inventors: Hui-Chun Wang, Kaohsiung (TW); Yang-Chang Wu, Kaohsiung (TW); Fang-Rong Chang, Kaohsiung (TW); Chin-Chung Wu, Kaohsiung (TW)

(73) Assignee: KAOHSIUNG MEDICAL UNIVERSITY, Kaosiung (TW)

( * ) Notice: Subject to any disclaimer, the term of this patent is extended or adjusted under 35 U.S.C. 154(b) by 0 days.

(21) Appl. No.: 15/883,741

(22) Filed: Jan. 30, 2018

(65) Prior Publication Data
US 2018/0161303 A1    Jun. 14, 2018

Related U.S. Application Data

(60) Division of application No. 15/016,690, filed on Feb. 5, 2016, now Pat. No. 9,918,962, which is a continuation-in-part of application No. 13/714,109, filed on Dec. 13, 2012.

(30) Foreign Application Priority Data

May 18, 2012    (TW) .............................. 101117920 A

(51) Int. Cl.
*A61K 31/352*    (2006.01)
*A61K 45/06*    (2006.01)
*C07D 309/30*    (2006.01)
*C07D 311/30*    (2006.01)
*C07D 311/78*    (2006.01)

(52) U.S. Cl.
CPC ............ *A61K 31/352* (2013.01); *A61K 45/06* (2013.01); *C07D 311/30* (2013.01); *C07D 311/78* (2013.01)

(58) Field of Classification Search
USPC ...................................................... 514/455
See application file for complete search history.

(56) References Cited

FOREIGN PATENT DOCUMENTS

| TW | I3211052 B | 3/2010 |
| TW | I324062 B | 5/2010 |

OTHER PUBLICATIONS

Andreassen et al., "ATR couples FANCD2 monoubiquitination to the DNA-damage response," Genes Dev. (2004) 18(16):1958-1963.
Chen HM et al., "A novel synthetic protoapigenone analogue, WYC02-9, induces DNA damage and apoptosis in DU145 prostate cancer cells through generation of reactive oxygen species," Free Radic Biol Med (2011) 50(9):1115-62.
Chen WY, et al., "Protoapigenone, a natural derivative of apigenin, induces mitogenactivated protein kinase-dependent apoptosis in human breast cancer cells associated with induction of oxidative stress and inhibition of glutathione S-transferase pi," Invest New Drugs (2011) 29(6): 1347-1359.
Chirnomas et al., "Chemosensitization to cisplatin by inhibitors of the Fanconi anemiafBRCA pathway," Mol Cancer Ther (2006) 5(4):952-61.
Chiu et al., "Fern plant-derived protoapigenone leads to DNA damage, apoptosis, and G(2)Im arrest in lung cancer cell line H1299," DNA Cell Biol (2009) 28(10):501-506.
Lopez-Contreras et al., "The ATR barrier to replication-born DNA damage," DNA Repair (Arnst) (2010) 9(12):1249-1255.
Nghiem et al., "ATR inhibition selectively sensitizes GI checkpoint-deficient cells to lethal premature chromatin condensation," Proc Natl Acad Sci USA (2001) 98(16):9092-9097.
Nitiss, "Targeting DNA topoisomerase II in cancer chemotherapy", Review, (2009) vol. 9, pp. 338-350.
Sorensen et al., "The cell-cycle checkpoint kinase Chkl is required for mammalian homologous recombination repair," Nat Cell Biol (2005) 7(2):195-201.
Wang et al., "Inhibition of ATR-dependent signaling by protoapigenone and its derivative sensitize cancer cells to interstrand cross-link-generating agents in vitro and in vivo," Mol Cancer Ther molcanther (2012) 11:1443-1453.

(Continued)

*Primary Examiner* — Kathrien A Cruz
(74) *Attorney, Agent, or Firm* — Volpe and Koenig, P.C.

(57) ABSTRACT

This invention is announcing a composition of flavonoid skeleton in the formula I or formula II compound, wherein each of the substituents is given the definition as set forth in the specification and claims. This composition have the capacity to treating or preventing a virus infection in a subject.

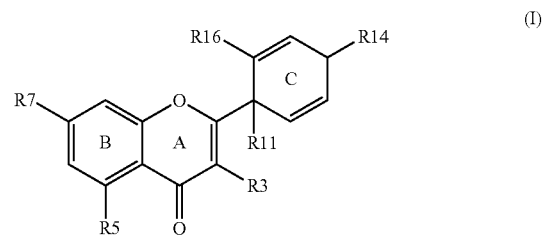

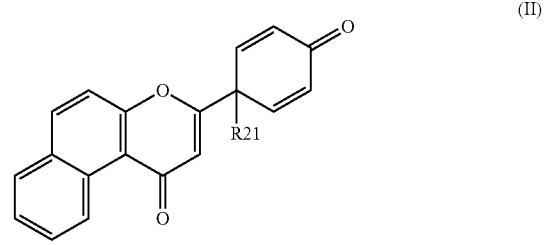

14 Claims, 41 Drawing Sheets
(5 of 41 Drawing Sheet(s) Filed in Color)
Specification includes a Sequence Listing.

(56) References Cited

OTHER PUBLICATIONS

Office Action dated Nov. 27, 2013 by the Taiwanese Patent Office.
Chaurushiya, (Viral Manipulation of DNA repair and cell cycle checkpoints, DNA Repair, 2009, 2;8(9); pp. 1166-1176).
Stropario, (Adenovirus Respiratory Infection: significant Increase in Diagnosis using PCR comparing with Antigen Detection and Culture Methods, Rev, Inst, Med. Trop>Sao Paulo, 52(6), pp. 317-321).
Lamarre, (An NS3 inhibitor with antiviral effects in humans infected with hepatitis C virus, Nature, 2003, 426, p. 186-189).

METHODS AND COMPOSITIONS FOR INHIBITION OF ATR AND FANCD2 ACTIVATION

CROSS REFERENCE TO RELATED APPLICATIONS

This application is a division of U.S. patent application Ser. No. 15/016,690, which was filed on Feb. 5, 2016 as a continuation-in-part of U.S. patent application Ser. No. 13/714,109, which was filed on Dec. 13, 2012 and claimed benefit of Taiwanese Patent Application No. 101117920, which was filed on May 18, 2012. All of the above applications are incorporated by reference herein as if fully set forth.

FIELD OF THE INVENTION

The application is related to the modulation of host cell factors required for DNA and RNA virus infections. Specifically, the application is related to benzopyran-4-one derivative compounds that target human host cell factors involved in DNA and RNA virus infections, and the use of such compounds to modulate DNA and RNA virus infections and as antiviral agents.

BACKGROUND OF THE INVENTION

The benzopyran-4-one derivative compound of formula I has a flavonoid moiety, which previously isolated and identified from the whole plant extract of *Thelypteris torresiana*, a fern species native to Taiwan.

The exposure and biological effects of Protoapigenone (I-1), 5',6'-Dihydro-6'-methoxy-protoapigenone (I-2) and Protoapigenin (I-3) compounds have been investigated by cytotoxicity assay. It was found Protoapigenone (I-1) demonstrated therapeutic effects and was a lead compound for potential anticancer drug development.

Furthermore, for developing a new potent anticancer drug, several analogues of I type compound such as I-4, I-5, I-6, I-7 and I-8, and another II type moiety such as II-1 and II-2 compound are also synthesized or semi-synthesized. Where the compound I-4 having chemical name 2-(1-hydroxy-4-oxocyclohexa-2,5-dienyl)-4H-chromen-4-one can be expressed by the general names of protoflavonone. The compound I-5 is also termed as 5-hydroxyprotoflavone, whose chemical name is 2-(1-hydroxy-4-oxocyclohexa-2,5-dienyl)-5-hydroxy-4H-chromen-4-one. The compound I-6 having chemical name 5-hydroxy-2-(1-hydroxy-4-oxocyclohexa-2,5-dienyl)-7-methoxy-4H-chromen-4-one can be expressed by the general names of 5-hydroxy-7-methoxy-protoflavonone. The homologous compounds I-4 and I-7 have the similar structure, but a different function group on R11 positions only, which is a hydroxyl group and another is methoxyl group in that position. The compound I-5, I-8, II-1 and II-2 also present the modified function group of R11 positions models.

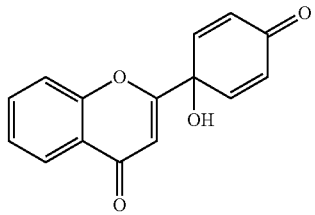

I-4

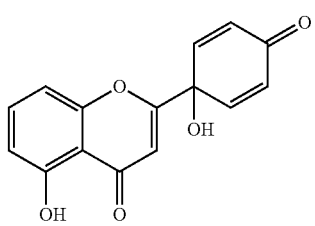

I-5

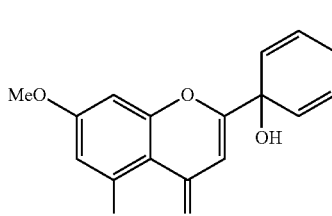

I-6

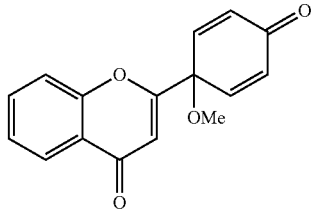

I-7

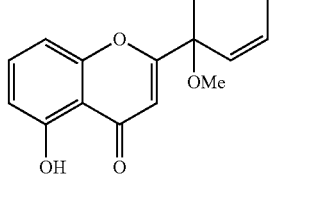

I-8

Formula II having an β-naphthoflavone moiety, the compound II-1 has chemical name 3-(1-hydroxy-4-oxo-cyclohexa-2,5-dienyl)-1H-benzo[f]chromen-1-one. Compound II-2 has chemical name 1'-methoxy-β-naphthoflavone.

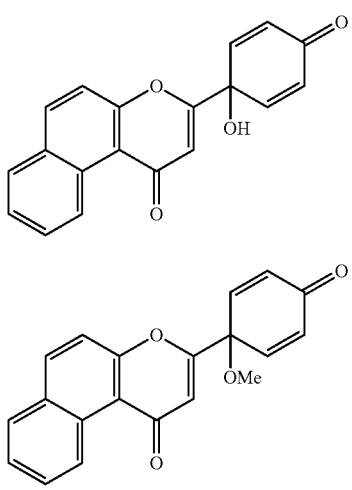

In previous studies, Protoapigenone (I-1) and its more potent analog compound II-1 (FIG. 1A) were shown to induce oxidative stress, consequently activating the p38 and JNK1/2 MAPK pathways following cell cycle arrest and apoptosis in several cancer cell types. These compounds were also found to reduce the size of tumor xenografts in nude mice without exerting toxic effects on the recipient. Recently, in those compounds of formula I and II were found to induce chromosomal breakage through oxidative stress, implicating a role for benzopyran-4-one derivatives of formula I and II in interfering with DNA metabolism. Up to date, the biomolecular actions and implications of this benzopyran-4-one derivatives mediated interference are mostly undetermined. Herein, we found that benzopyran-4-one derivatives are capable of inhibiting DNA damage-induced activation of ATR targets Chk (Cell Cycle Checkpoint Kinase) 1 and FANCD2, which then sensitize tumor cells to chemotherapy, and finally results in tumor size reduction in mice.

During virus infection, the immune system of the host is typically activated for defense. However, once it enters into a host cell, the virus will exploit some of the host cell's machinery to replicate themselves at high speed. Several types of viruses have shown this replication, including the DNA viruses Epstein-Barr virus (EBV), herpes simplex virus 1 (HSV-1), adenovirus and SV40, papilloma virus, Hepatitis B virus, sindbis virus, and the lentivirus human immunodeficiency virus (HIV), which lead to the activation of host DNA-damage response pathways. The activation of cellular DNA repair and recombination enzymes is beneficial for viral replications. Further, research shows that new small-molecule inhibitors of the DNA-damage response pathways may be of value to treat viral infections.

Strategies for identifying targets for antiviral intervention typically focus on compounds that attack the viral proteins including the structural components of the virion as well as viral genome-encoded enzymes which are necessary for propagation of the virus. The approach of targeting viral proteins has several limitations: i) the limited number of viral targets; ii) viral targets tend to be highly specific to a particular virus or even strain of virus; and iii) viruses are able to rapidly alter their genetic composition to develop resistance to antiviral drugs. Another approach in antiviral drug development is to design drugs to strengthen the host's factors to fight the viral infection, rather than to fight the viral infection itself.

Our results show that these benzopyran-4-one derivatives compounds are noteworthy potential to treat virus infection by the inhibition of ATR signaling cascades.

SUMMARY OF THE INVENTION

The application is related to methods of treating DNA and RNA virus infections and methods of treating or preventing a symptom or disease associated with DNA and RNA virus infection, comprising administering to a subject a composition comprising a benzopyran-4-one derivative compound that targets a human host cell factor involved in DNA and RNA virus infections.

The present application is based, in part, on the discovery that virus infections can be reduced by pharmacologically targeting human host cell factors required for viral replications. Targeting host cell factors, rather than the viral factors required for influenza virus replication, may greatly reduce the emergence of viral resistance and expand the number of targets for antiviral intervention.

Disclosed herein are benzopyran-4-one derivative compounds that target human host cell factors involved in virus infection and replication. Disclosed herein are pharmaceutical compositions, comprising such compounds, and methods of using such compounds to modulate the virus infection and replication. In some embodiments, the compounds and compositions comprising them reduce or inhibit virus infection and replication. Disclosed herein are methods of using such compounds and compositions to reduce or inhibit virus infection and replication. In some embodiments, the compounds modulate virus infection and replication by altering the expression of, e.g., mRNA or protein and/or activity of the human host cell factors (e.g., ATR and FANCD2) involved in the virus infection and replication. In some embodiments, the compounds reduce or inhibit virus infection and replication by reducing or inhibiting the expression of mRNA or protein and/or activity of the human host cell factors involved in the virus infection and replication. In some embodiments, the human host cell factor interacts with a component of the DNA and/or RNA viruses. In some embodiments, the human host cell factor is required for the virus infection and replication.

The compounds disclosed herein, and for use in the compositions and methods disclosed herein, target human host cell factors involved in DNA and RNA viruses and modulate DNA and RNA viruses. In some embodiments, the compounds disclosed herein, and for use in the compositions and methods disclosed herein, target human host cell factors involved in DNA and RNA viruses and reduce or inhibit DNA and RNA viruses. The targeted human host cell factors may be required for DNA and RNA viruses. The targeted human host cell factors may be involved in or required for one or more of the following events of the viral life cycles: entry; uncoating; nuclear import; viral RNA transcription; or viral RNA translation. The targeted human host cell factor may be involved in or required for replication of more than one strain of DNA and RNA viruses. For example, the human host cell factor may be involved in or required for infection and replication of viruses including: double-stranded DNA viruses (Adenoviruses, Herpesviruses, Poxviruses, etc.); single-stranded (+)sense DNA viruses (Parvoviruses); double-stranded RNA viruses (Reoviruses and Birnaviruses); single-stranded (+)sense RNA viruses (Picornaviruses, Togaviruses, etc.); single-stranded (−)sense RNA viruses (Orthomyxoviruses, Rhabdoviruses, etc.); single-stranded (+)sense RNA viruses with DNA intermediates in the life-cycle (Retroviruses); and double-stranded DNA viruses with RNA intermediates in the life-cycle (Hepadnaviruses).

In some embodiments, a compound disclosed herein, and for use in the compositions and methods disclosed herein, targets a component or regulator of, or factor that interacts with, one or more of the following categories of human host cell factors: cytoskeleton; ribonucleoprotein; spliceosome; ubiquitin/proteasome system; ribosome or other translation machinery; kinase; phosphatase; signaling (e.g., G-protein coupled receptors and signaling at the plasma membrane); mitochondrion or mitochondrial ribosome; plasminogen; stress response; v-ATPase; ion channel or other ion transport; nucleus; sumoylation; nuclear transport; nucleotide binding; cell cycle; vesicular transport (e.g., COPI vesicle); chromosome; carboxylic acid metabolism; DNA damage response; or DNA repair. In some embodiments, a compound disclosed herein, and for use in the compositions and methods disclosed herein, targets a component or regulator of, or a factor that interacts with, one or more of the following categories of human host cell factors: ATR-Chk1 pathway; ATM-Chk2 pathway; MRN (Mre11-Rad50-Nbs1) complex; histone H2AX; MCPH1/BRIT1; CTIP; SMC1; IP3-PKC pathway; COPI vesicles; endosomal uptake, maturation, acidification, and fusion; actin organization and function; PI3K-AKT pathway; endosomal recycling pathway; MAPK pathway; proteases; calcium/calmodulin system; nuclear trafficking; trafficking; sumoylation; microtubule organization (including assembly) and function; autophagy; and ubiquitination.

In some embodiments, a compound disclosed herein, and for use in the compositions and methods disclosed herein, targets a component or regulator of, or factor that interacts with, one or more of the following categories of human host cell factors: the base excision repair proteins UNG, SMUG1, MBD4, TDG, OGG1, MYH, NTH1, MPG, NEIL1, NEIL2 and NEIL3 (DNA glycosylases); APE1 or APEX2 (AP endonucleases); LIG1 or LIG3 (DNA ligases I and III); XRCC1 (LIG3 accessory); PNK or PNKP (polynucleotide kinase and phosphatase); PARP1, PARP2 (Poly(ADP-Ribose) Polymerases); PolB or PolG (polymerases); FEN1 (endonuclease) and Aprataxin.

In some embodiments, a compound disclosed herein, and for use in the compositions and methods disclosed herein, targets a component or regulator of, or factor that interacts with, one or more of the base excision repair proteins PARP1, PARP2, and PolB. In other embodiments, the base excision repair protein is PARP1 or PARP2.

Yet another embodiment provides use of benzopyran-4-one derivative compounds as a single agent (monotherapy) for treating virus. In some embodiments, the benzopyran-4-one derivative compounds are used to treat patients having a virus infection in combinational therapy. In other embodiments, said combinational therapy uses at least two composition formulas of the composition.

In some embodiments, the compound is an agent that reduces or inhibits the expression of mRNA or protein and/or activity of a human host cell factor involved in virus infection and replication. In some embodiments, the compound reduces or inhibits the interaction of a human host cell factor with a component of the viruses. In some embodiments, the compound reduces or inhibits one or more of the following events of the DNA and RNA viral life cycle: entry; uncoating; nuclear import; viral RNA transcription; and viral RNA translation. In some embodiments, the compound reduces or inhibits replication of more than one strain of DNA or RNA viruses. For example, the compound may reduce or inhibit infection and replication of viruses, such as double-stranded DNA viruses (Adenoviruses, Herpesviruses, Poxviruses, etc.); single-stranded (+)sense DNA viruses (Parvoviruses); double-stranded RNA viruses (Reoviruses and Birnaviruses); single-stranded (+)sense RNA viruses (Picornaviruses, Togaviruses, etc.); single-stranded (−)sense RNA viruses (Orthomyxoviruses, Rhabdoviruses, etc.); single-stranded (+)sense RNA viruses with DNA intermediates in the life-cycle (Retroviruses); and double-stranded DNA viruses with RNA intermediates in the life-cycle (Hepadnaviruses).

In accordance with an aspect of the present invention, compounds of benzopyran-4-one derivatives, characteristically with inhibiting of DNA Damage Response (DDR), are provided. The benzopyran-4-one derivatives includes a common structure being the following formula I:

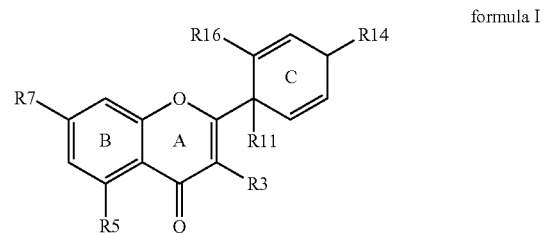

formula I wherein: $R_3$, $R_5$, $R_7$, $R_{11}$, $R_{14}$ and $R_{16}$ are selected independently from a group consisting of a hydrogen, a hydroxyl group, a methoxyl group and a oxygen atom contain a double bond.

In accordance with a further aspect of the present invention, compounds of benzopyran-4-one derivatives, characteristically with ATR-mediated DNA damage checkpoint, is provided. The benzopyran-4-one

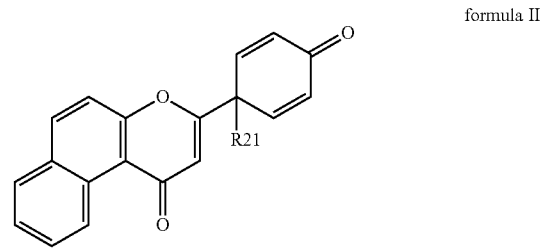

formula II derivatives includes a common structure being the following formula II;
wherein: $R_{21}$ is selected independently from a group consisting of a hydrogen, a hydroxyl group and a methoxyl group.

In a further aspect of the present invention, a method for assaying a state of DNA DDR kinase signaling cascades is provided. The method includes steps of:
providing a reaction site thereof;
adding to the reaction site an effective amount of a benzopyran-4-one derivative represented by one of formula I and formula II,

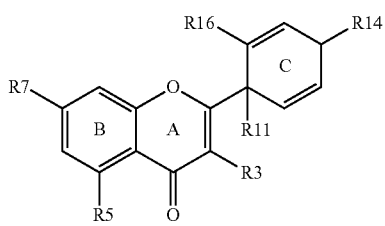

formula I

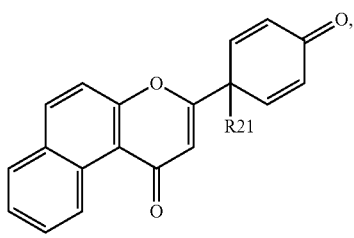

formula II wherein each of $R_3$, $R_5$, $R_7$, $R_{11}$, $R_{14}$, and $R_{16}$ is one selected from a group consisting of a hydrogen, a hydroxyl group, a methoxyl group and a oxygen atom containing a double bond. $R_{21}$ is one selected from a group consisting of a hydrogen, a hydroxyl group and a methoxyl group.

In a further aspect of the present invention, a method for treating or preventing a virus infection in a subject is provided. The method comprises a step of administering to the subject with the virus infection a therapeutically effective amount of a benzopyran-4-one derivative for a administration duration between 1 to 10 days to inhibit a viral replication in the subject.

In a further aspect of the present invention, a method for inhibiting replication of a virus in a subject is provided. The method comprises a step of administering to the subject at risk of developing a viral infection a therapeutically effective amount of a benzopyran-4-one derivative at an interval selected from a group consisting of a once-daily interval, a multiple-daily interval and a weekly interval.

In a further aspect of the present invention, a method for dealing with a virus infection in a subject, comprising steps of identifying the subject with the virus infection; and administering to the subject infected by a virus a therapeutically effective amount of a benzopyran-4-one derivative.

The above objects and advantages of the present aspects will become more readily apparent to those ordinarily skilled in the art after reviewing the following detailed descriptions and accompanying drawings.

BRIEF DESCRIPTION OF THE DRAWINGS

The patent or application file contains at least one color drawing or photograph as a drawing executed in color. Copies of this patent or patent application publication with color drawing(s) will be provided by the Office upon request and payment of the necessary fee.

FIG. 3(a) illustrates immunoblots showing the expression of MDA-MB-231 cell.

FIG. 3(b) illustrates immunoblots showing the expression of A549 cell.

FIG. 5(a) illustrates immunoblots showing the expression of inhibiting Chk1 phosphorylation.

FIG. 5(b) illustrates immunoblots showing the expression of A549 cell. Cells are pretreated with 50 μM okadaic acid (OA) or 20 μM MG132 and subjected to 10 J/m² UV for 1 h to induce DDR.

FIG. 6(a) illustrates immunoblots showing the expression of A549 cell.

FIG. 6(b) illustrates immunoblots showing the expression of MDA-MB-231 cell. Cells are pretreated with chemicals for 20 min and subjected to 10 J/m² UV for 1 h to induce DDR.

FIG. 8(a) illustrates immunoblots showing the expression DDR induced by $H_2O_2$ (peroxide).

FIG. 8(b) illustrates immunoblots showing the expression DDR induced by hydroxyurea (HU).

FIG. 10(a) illustrates immunoblots showing compound I-1 inhibit $H_2O_2$-induced Chk1 phosphorylation.

FIG. 10(b) illustrates immunoblots showing compound I-1 inhibit UV-induced Chk1 phosphorylation.

FIG. 10(c) illustrates immunoblots showing compound II-1 inhibit $H_2O_2$-induced Chk1 phosphorylation.

FIG. 12(a) illustrates percentages of the mitotic marker.

FIG. 12(b) illustrates the expression FACS (Fluorescence Activated Cell Sorting) dot blot for analyzing the percentage of GFP cell denoting the HRR frequency.

FIG. 14(a) illustrates immunoblots showing the effect on cisplatin-induced DDR in A594 cell.

FIG. 14(b) illustrates immunoblots showing the effect on cisplatin-induced DDR in U2OS cell.

FIG. 14(c) illustrates immunoblots showing the effect on cisplatin-induced DDR in MDA-MB-231 cell.

FIG. 15(a) illustrates the effects fraction of compound I-1.
FIG. 15(b) illustrates the effects fraction of compound II-1.

FIG. 16(a) illustrates the effects fraction of compound I-1.
FIG. 16(b) illustrates the effects fraction of compound II-1.

FIG. 17(a) illustrates the effects fraction of compound I-1.
FIG. 17(b) illustrates the effects fraction of compound II-1.

FIG. 19(a) illustrates the effects on A549 cells
A—control
B—0.25 µM compound I-1
C—0.5 µM compound I-1
D—1 µM compound I-1
FIG. 19(b) illustrates the effects on MDA-MB-231 cells
A—control
B—0.25 µM compound I-1
C—0.5 µM compound I-1
D—1 µM compound I-1

FIG. 20(a) illustrates the effects of compound I-1.
A—control
B—0.1 µM compound II-1
C—0.2 µM compound II-1
D—0.4 µM compound II-1
FIG. 20(b) illustrates the effects of compound II-1.
A—control
B—0.1 µM compound II-1
C—0.2 µM compound II-1
D—0.4 µM compound II-1

FIG. 21(a) illustrates the effects of unsynchronized cells.
FIG. 21(b) illustrates the effects of control group.

FIG. 22(a) illustrates the effects of control group.
FIG. 22(b) illustrates the effects of compound I-1.
FIG. 22(c) illustrates the effects of compound II-1.

FIG. 23(a) illustrates the effects of control group.
FIG. 23(b) illustrates the effects of compound I-1.
FIG. 23(c) illustrates the effects of compound II-1.

FIG. 24(a) illustrates the effects of DMSO group.
FIG. 24(b) illustrates the effects of Hydroxyurea (HU) group.
FIG. 24(c) illustrates the effects of ku55933 group.
FIG. 24(d) illustrates the effects of compound I-1.
FIG. 24(e) illustrates the effects of compound II-1.

DETAILED DESCRIPTION OF THE PREFERRED EMBODIMENT

Figure 1:
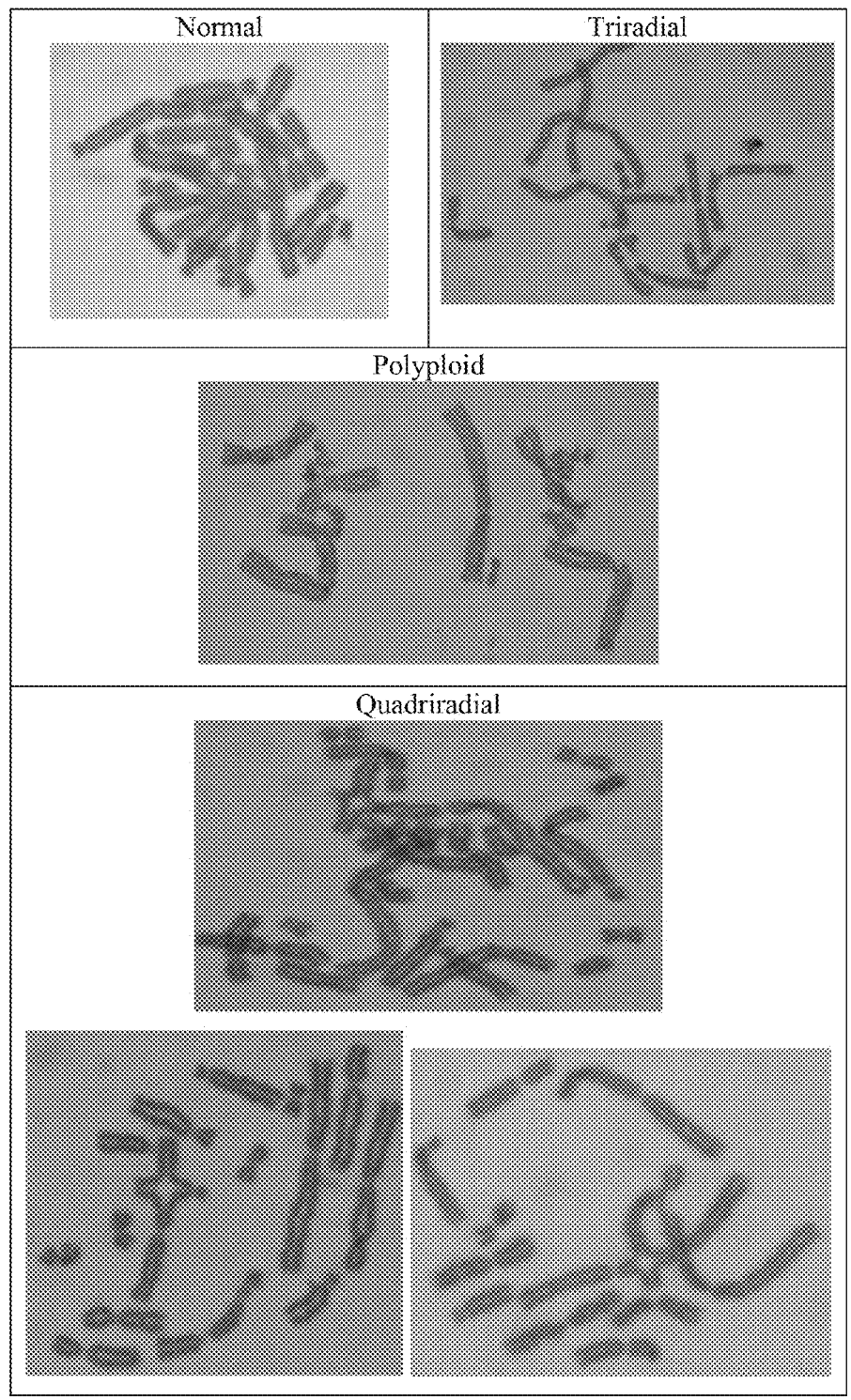
FIG. 1 illustrates Protoapigenone (I-1) induce chromosome aberration but does not produce marked DDR.

Further embodiments herein may be formed by supplementing an embodiment with one or more element from any one or more other embodiment herein, and/or substituting one or more element from one embodiment with one or more element from one or more other embodiment herein.

The phrase "virus infection" in this disclosure refers to DNA virus infection, RNA virus infection or both of them, and the term "virus" in this disclosure refers to DNA virus, RNA virus or both of them.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Ataxia telangiectasia-mutated (ATM) and ATM and Rad3-related (ATR) are 2 members of the phosphoinositide 3-kinase (PI3K)-related protein kinases family that play a central role in DNA damage response (DDR) coordination; they also function in the signaling cascades machinery of cell cycle arrest, DNA repair and transcription, and cell death. While ATM is predominant activated in response to DNA strand breaks, ATR is activated in response to damage arising from ultraviolet (UV) ray or replication block; both kinases activate signaling cascades that involving 2 checkpoint kinases effectors, Chk1 and Chk2, whose roles were previously suggested to be redundant. In contrast to ATM, ATR has been reported to be indispensible for cell growth and for life. ATR-knockout mouse embryos died early due to mitotic catastrophe characterized by incomplete DNA replication and chromosomal fragmentation. Moreover, ATR gene mutations are rarely found in humans. The only mutated variants that can survive are heterozygous or hypomorphic variants. Furthermore, cells derived from patients with Seckel syndrome exhibit cellular features associated with ATR signaling cascades defects. Consistent with this phenotype, seckel-like mouse embryonic cells showed accelerated aging due to replicative stress, exhibiting an accumulation of lethal chromosomal breaks. However, with regard to its role in regulating the replication checkpoint, ATR is activated by most cancer chemotherapeutic agents that target DNA in replicating cells. Therefore, inhibition of ATR signaling cascades is a valid and promising strategy that can improve chemotherapeutic or radiotherapeutic efficiency.

Thus so far, several inhibitors of DDR-related kinases, including Chk1 and Chk2, have been successfully used alone or in combination with each other in clinical trials. Recently, several chemicals that inhibit ATR kinase activity in vitro were used to support the hypothesis that ATR kinase can be targeted to improve cancer therapy. Since most of these studies are in their initial stages, it is imperative to focus more efforts toward investigating strategies to inhibit ATR signaling cascades.

In accordance with an aspect of the present invention, benzopyran-4-one derivatives compound, characteristically with inhibiting of DNA Damage Response (DDR), is provided.

Another aspect of this invention, pharmaceutical composition of benzopyran-4-one derivatives, characteristically with inhibiting of DNA Damage Response (DDR), is provided. The benzopyran-4-one derivatives includes a common structure being the following formula I or formula II,

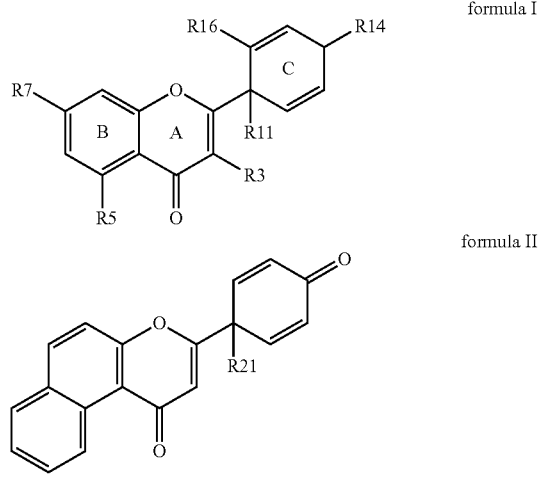

wherein: $R_3$, $R_5$, $R_7$, $R_{11}$, $R_{14}$ and $R_{16}$ are selected independently from a group consisting of a hydrogen, a hydroxyl group, a methoxyl group and a oxygen atom contain a double bond. $R_{21}$ is selected independently from a group consisting of a hydrogen, a hydroxyl group and a methoxyl group.

In a further aspect of this invention is directed towards a method of treating cancer in a subject in need thereof, including the sequential or simultaneous co-administration of a compound of benzopyran-4-one derivatives or a pharmaceutically acceptable salt thereof, and a DNA-damaging agent. In some embodiments, said DNA-damaging agent is selected from chemotherapeutic drugs such as alkylating agents, antimetabolic agents, antibiotic anti-cancer agents, Topoisomerase inhibitors and anti-mitosis agents.

In some embodiments, said alkylating agent is one selected from Nitrogen mustards (eg. Melphalan, mechlorethamine, Chlorambucil, Ifosfamide, Cyclophosphamide, Estramustine and phenoxybenzamine); or Aziridines (eg. Thiotepa, Carboquone); or Nitrosoureas (eg. Carmustine, Semustine, Iomustine, Nimustine, Streptozocin, Ranimustine and Lomustine); or Procarbazine and triazenes (eg. Dacarbazine, Temozolomide and Procarbazine); or Alkyl sulfonate (eg. Busulfan); or Platinum coordination complex (eg. Cisplatin, Carboplatin, Nedaplatin, Iproplatin and Oxaliplatin); and mixtures thereof.

In some embodiments, said antimetabolic agents are one selected from Thymidylate synthase inhibitor (eg. Aminopterin, Methotrexate, Tegafur, Piritrexin, Trimetrexate, Floxuridine, Raltitrexed, Pemetrexed, Fluorouracil, Doxifluridine and Capecitabine); or Amidophosphoribosyl transferase inhibitors (eg. Mercaptopurine, Thioguanine and Thionosine); or DNA chain elongation inhibitors (eg. Cytarabine, Ancitabine, Gemcitabine, Fludarabine, Cladribine, Clofarabine, Azaserine, Azacitidine, Pentostatin, Hydroxyurea); and mixtures thereof.

In some embodiments, said antibiotic anti-cancer agent is one selected from free radical agents (eg. Bleomycin and Actinomycin D); or Topoisomerase II inhibitors (eg. Daunorubicin, Doxorubicin, Idarubicin, Epirubicin, valrubicin, Pirarubicin, Aclarubicin, Mitoxantroneand Piroxanthrone); or other therapies or anticancer agents (eg. Menogaril, Plicamycin, Acivicin, Anthramycin, Pentostatin, Calicheamicin and Peplomycin); and mixtures thereof.

In some embodiments, said Topoisomerase inhibitor is one selected from Topoisomerase I inhibitors (eg. Camptothecin, Irinotecan, Topotecan); or Topoisomerase II (eg. Podophyllin, Podophyllotoxin, Etoposide, Teniposide); and mixtures thereof.

In some embodiments, said anti-mitosis agent is one selected from Paclitaxel and Docetaxel; or anti-microtubule agents (eg. Colchicine, Vinblastine, Vincristine, Vindesine and Vinorelbine); and mixtures thereof.

Benzopyran-4-one derivatives compounds of this invention include Protoapigenone (I-1), 5',6'-dihydro-6'-methoxy-protoapigenone (I-2), Protoapigenin, (I-3), protoflavonone (I-4), 5-hydroxyprotoflavone (I-5), 5-hydroxy-7-methoxy-protoflavonone (I-6), compounds I-7, compounds I-8, 3-(1-hydroxy-4-oxocyclohexa-2,5-dienyl)-1-H-benzo[f]chromen-1-one (II-1) and compounds II-2.

In a further aspect of this invention, pharmaceutical composition of benzopyran-4-one derivatives, characteristically with modulating the activation state of ATM kinase is provided. The benzopyran-4-one derivatives includes a common structure being the following formula I or formula II,

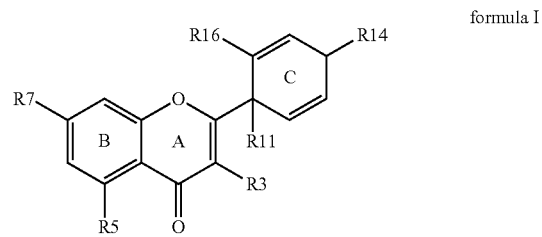

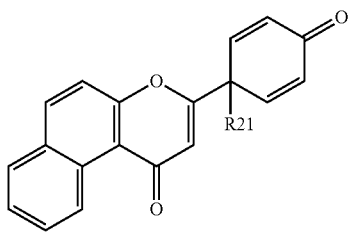

formula II

In a further aspect of this invention, both assay kit and assay composition of benzopyran-4-one derivatives, characteristically with detecting the activation state of ATR, DNA DDR kinase signaling cascades is provided.

In a further aspect of this invention is directed towards a method of analyzing ATR, DNA DDR kinase signaling cascades in a reaction site thereof, including the sequential or simultaneous of benzopyran-4-one derivatives compound or a pharmaceutically acceptable salt thereof, and a chemotherapeutic drugs or additional agent. In some embodiments, said chemotherapeutic drug is selected from chemotherapeutic drugs such as alkylating agents, antimetabolic agents, antibiotic anti-cancer agents, Topoisomerase inhibitors and anti-mitosis agents.

In some embodiments, the individual components of the combination may be administered separately, at different times during the course of therapy, or concurrently, in divided or single combination forms. Also provided is, for example, simultaneous, staggered, or alternating treatment.

In a further aspect of this invention, compounds and pharmaceutical composition of benzopyran-4-one derivatives, characteristically with detecting of DNA damage in cancer cell as determined by the activation state of ATM kinase is also useful for monitoring therapeutic effects during treatment.

In some embodiments, method using benzopyran-4-one derivatives compound or pharmaceutical composition for defecting in the ATR signaling cascade and/or DNA-damage response (DDR). In some embodiments, said defect is altered expression or activity of one or more of the following cell markers as determined by standard cell marker detection assays: ATM, CHK1, CHK2, cellular tumor antigen p53, Adenosine monophosphate activated protein kinase (AMPK), mammalian target of rapamycin complex (mTORC) 1, metal response element (MRE) 11, mitogen-activated protein kinase (MAPK), MAPK-activated protein kinase (MAPKAPK) 2, DNA Repair Protein (RAD50), Nijmegen breakage syndrome (NBS) 1, 53BP1, mediator of DNA damage checkpoint (MDC) 1, H2A histone family member X (H2AX).

In another embodiment, the cell is a cancer cell expressing DNA damaging oncogenes. In some embodiments, said cancer cell has altered expression or activity of one or more of the following cell markers as determined by standard cell marker detection assays: K-Ras, N-Ras, H-Ras, Raf, Myc, Mos, E2F, Cdc25A, CDC4, CDK2, Cyclin E, Cyclin A and Rb.

In a further embodiment, the invention relates to an assay kit or assay composition for determent of ATR and/or DNA DDR signaling cascades at reaction site. In particular the assay kit or assay composition can include, a benzopyran-4-one derivatives compound, a processing/handling plan, a compartment, a additional reagent and instructions for use, or a reagent with a compartment and instructions for use. In one embodiment, for the purpose of altered expression or activity can then generate a detectable at the reaction site of the immunocomplex.

The additional reagent can include ATR, the ATR receptor, the complex of DNA, or an antigenic fragment thereof, a binding composition, or a nucleic acid. A kit for determining the binding of a test compound, e.g., acquired from a biological sample or from a chemical library, can include a control compound, a labeled compound, and a method for separating free labeled compound from bound labeled compound and a combination thereof.

The term excipients or "pharmaceutically acceptable carrier or excipients" and "bio-available carriers or excipients" above-mentioned include any appropriate compounds known to be used for preparing the dosage form, such as the solvent, the dispersing agent, the coating, the anti-bacterial or anti-fungal agent and the preserving agent or the delayed absorbent. Usually, such kind of carrier or excipient does not have the therapeutic activity itself. Each formulation prepared by combining the derivatives disclosed in the present invention and the pharmaceutically acceptable carriers or excipients will not cause the undesired effect, allergy or other inappropriate effects while being administered to human. Accordingly, the derivatives disclosed in the present invention in combination with the pharmaceutically acceptable carrier or excipients are adaptable in the clinical usage and in the human. A therapeutic effect can be achieved by using the dosage form in the present invention by the local or sublingual administration via the venous, oral, and inhalation routes or via the nasal, rectal and vaginal routes. About 0.1 mg to 1000 mg per day of the active ingredient is administered for the patients of various diseases.

The carrier is varied with each formulation, and the sterile injection composition can be dissolved or suspended in the non-toxic intravenous injection diluents or solvent such as 1,3-butanediol. Among these carriers, the acceptable carrier may be mannitol or water. Besides, the fixing oil or the synthetic glycerol ester or di-glycerol ester is the commonly used solvent. The fatty acid such as the oleic acid, the olive oil or the castor oil and the glycerol ester derivatives thereof, especially the oxy-acetylated type, may serve as the oil for preparing the injection and as the naturally pharmaceutical acceptable oil. Such oil solution or suspension may include the long chain alcohol diluents or the dispersing agent, the carboxylmethyl cellulose or the analogous dispersing agent. Other carriers are common surfactant such as Tween and Spans or other analogous emulsion, or the pharmaceutically acceptable solid, liquid or other bio-available enhancing agent used for developing the formulation that used in the pharmaceutical industry.

The composition for oral administration adopts any oral acceptable formulation, which includes capsule, tablet, pill, emulsion, aqueous suspension, dispersing agent and solvent. The carrier generally used in the oral formulation, taking a tablet as an example, the carrier may be lactose, corn starch and lubricant, and magnesium stearate is the basic additive. The excipients used in a capsule include lactose and dried corn starch. For preparing an aqueous suspension or an emulsion formulation, the active ingredient is suspended or dissolved in oil interface in combination with the emulsion or the suspending agent, and appropriate amount of sweetening agent, flavors or pigment is added as needed.

The nasal aerosol or inhalation composition may be prepared according to the well-known preparation techniques. For example, the bioavailability can be increased by dissolving the composition in the phosphate buffer saline and adding the benzyl alcohol or other appropriate preservative, or the absorption enhancing agent. The compound of the present invention may be formulated as suppositories for rectal or virginal administration.

The compound of the present invention can also be administered intravenously, as well as subcutaneously, parentally, muscular, or by the intra-articular, intracranial, intra-articular fluid and intra-spinal injections, the aortic injection, the sterna injection, the intra-lesion injection or other appropriate administrations.

Protoapigenone (I-1) induces chromosomal aberrations but does not produce marked DDR.

Previously, Protoapigenone (I-1) and compound II-1 were demonstrated to cause DNA strand breaks and apoptosis in lung and prostate cancers (Chen H M, et al., Free Radic Biol Med 2011), suggesting that inducing DNA damage may be the potential mechanism underlying the anticancer effect of benzopyran-4-one derivatives.

To test this hypothesis, we investigated the cytogenetic effect of Protoapigenone (I-1) on CHO cells (FIG. 1). According to the Table 1, low Protoapigenone (I-1) concentrations produced dose-dependent increases in chromosomal structural changes, such as breakages, radials, and chromosomal polyploidy, similar to the effects seen with mitomycin C treatment; however, the complete mitotic chromosome could not be obtained upon high-dose Protoapigenone (I-1) treatment.

TABLE 1

Protoapigenone (I-1) induces chromosomal aberration in CHO cells

| Treatment | DMSO control | Protoapigenone (I-1) | mitomycin C |
|---|---|---|---|
| Concentration (µM) | 0.00 | 2.17 | 4.35 | 2.00 |
| chromatid break (No.) | 0 | 2 | 1 | 2 |
| Chromatid deletion | 0 | 0 | 1 | 3 |
| Triradial | 0 | 4 | 13 | 42 |
| quadriradial | 0 | 3 | 9 | 29 |
| ring | 0 | 1 | 2 | 0 |
| complex rerrangement | 0 | 0 | 0 | 2 |
| dicentric | 0 | 0 | 0 | 1 |
| polyploid | 1 | 3 | 1 | 0 |
| pulverized cell | 0 | 0 | 1 | 5 |
| Average aberrant metaphases (%)[a] | 0.5 | 6.5 * | 14.0 * | 42.0 * |

Note:
1. Two hundred cells per treatment were analysized for chromosomal aberration.
2. Type of structural aberrations, such as chromatid break, chromatid deletion, triradial, quadriradial, ring, complex rerrangement, dicentric, polyploid and pulverized cell numbers (No.) were indicated.
3. Others chromosome gap, chromosome break, chromosome deletion and chromatid gap were not be observed in this experiment.
4. [a], * indicated statistic significantly for tested vs. control group by t-test.

Figure 2:
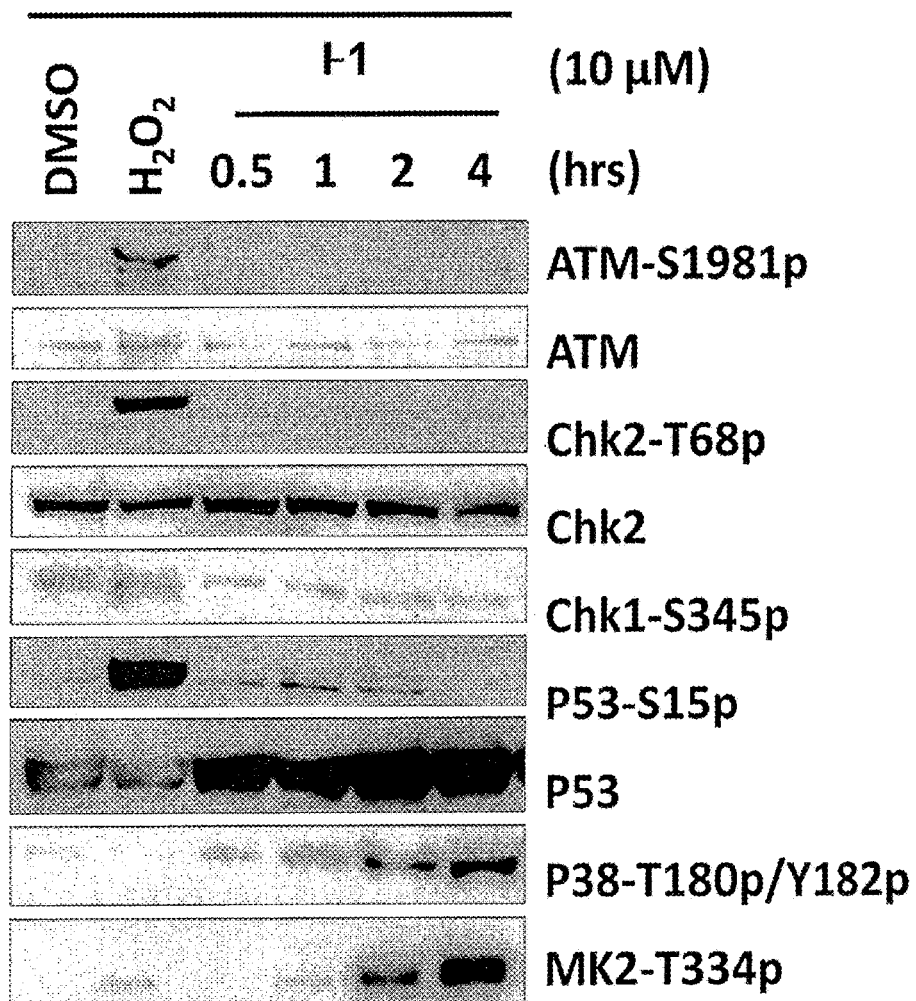
FIG. 2 illustrates immunoblots showing DDR by detecting phosphorylation of cell marker following exposure of HEK293T cell to 10 μM compound I-1 for the indicated times.
Figure 3A:
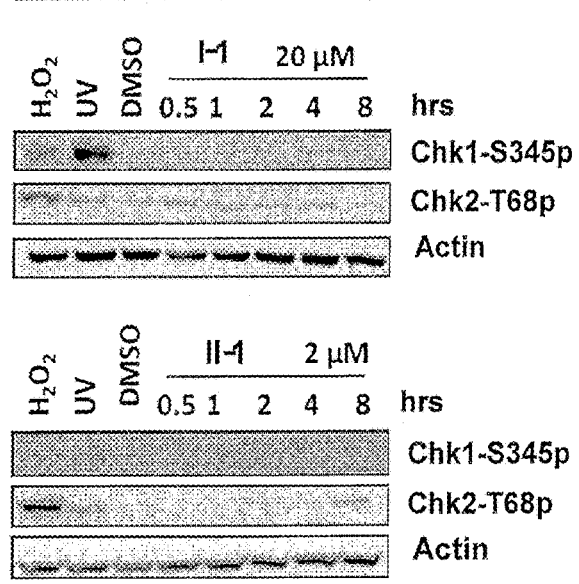
FIGS. 3(a)-3(b) show that dose-dependent effects of compound I-1 and compound II-1 on the inhibition of UV-induced Chk1 phosphorylation in cells.
Figure 3B:
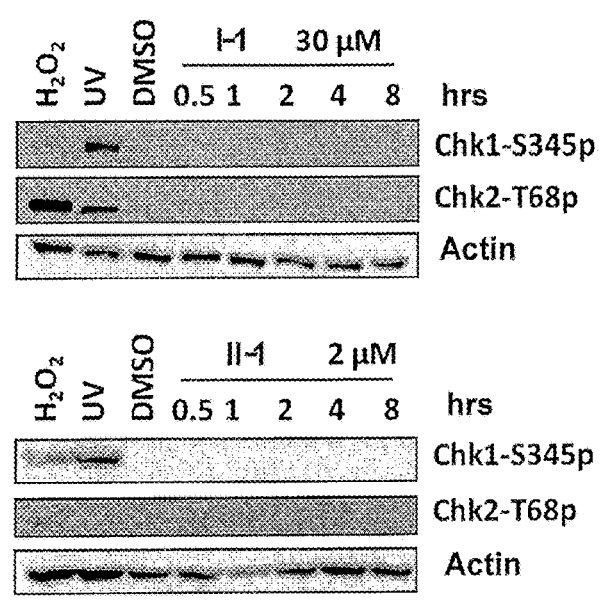
Figure 4:
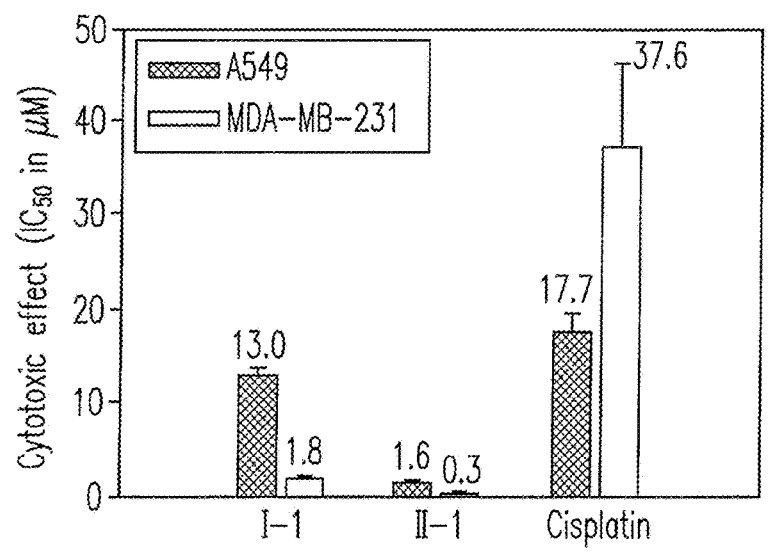
FIG. 4 shows the cytotoxic effect of compound against cell line.

Since mitomycin C can induce DDR in many cancers, we investigated what kind of DDR signaling was activated by Protoapigenone (I-1). Surprisingly, high doses of Protoapigenone (I-1) in HEK293T cells did not induce noticeable changes in the putative DDR signaling, which we measured by analyzing the phosphorylation of the ATM-dependent Chk2 Thr[68] residue and the ATR-dependent Chk1 Ser[345] residue (FIG. 2). We did observe that Protoapigenone (I-1) treatment caused slight accumulation of the p53 protein, which could have been the result of several posttranslational modifications. However, phosphorylation of the p53 Ser[15] residue did not contribute to this Protoapigenone (I-1)-induced p53 protein accumulation, suggesting that Protoapigenone (I-1) does not directly damage DNA because DNA damage normally stimulates ATM/ATR-dependent p53 Ser15 phosphorylation. Our result is similar to previous reports that p38 MAPK is activated by Protoapigenone (I-1) (Chen W Y, et al. Invest New Drugs 2011), as its downstream target MAPKAPK2 was found to be phosphorylated starting as early as 2 h after Protoapigenone (I-1) exposure (FIG. 2). We repeated the benzopyran-4-one derivatives experiment on lung and breast carcinoma cell lines A549 and MDA-MB-231 cells, respectively, and obtained similar results. Consistently, no marked changes in Chk1 and Chk2 phosphorylation signaling were detected even at high doses of either drug for as long as 8 h after drug treatment (FIGS. 3(a) and 3(b)). The cytotoxic effect by benzopyran-4-one derivatives on cancer cells was determined by MTT assay at 48 h of incubation (FIG. 4); our data indicated that the $IC_{50}$ value range for cytotoxicity was similar to those in previous reports, confirming that benzopyran-4-one derivatives are stable compounds that do not directly cause DNA damage.

Protoapigenone (I-1) and Compound II-1 Inhibit Chk1 Phosphorylation after DNA Damage.

Figure 5A:
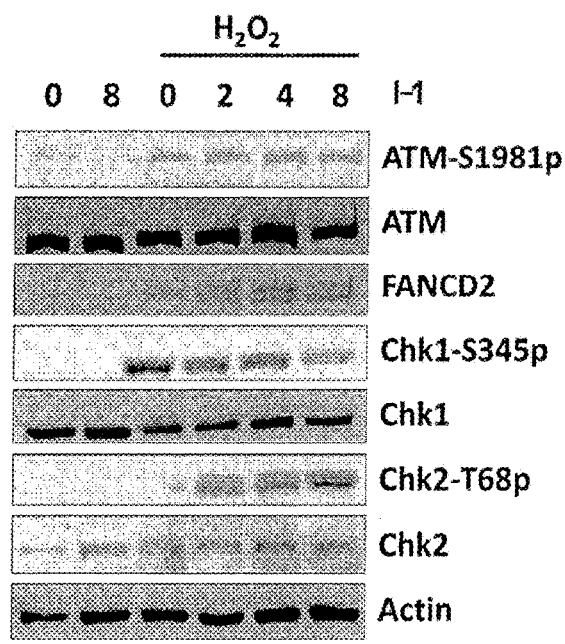
FIGS. 5(a)-5(b) show benzopyran-4-one derivatives inhibit DNA damage-induced DDR.
Figure 5B:
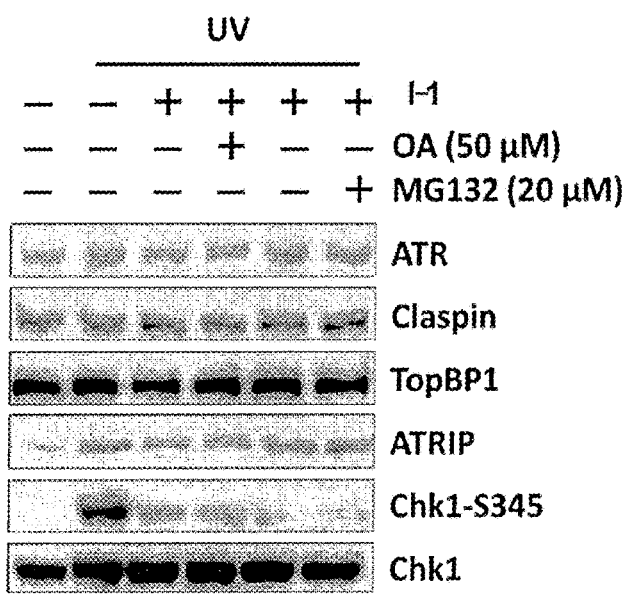
Figure 6A:
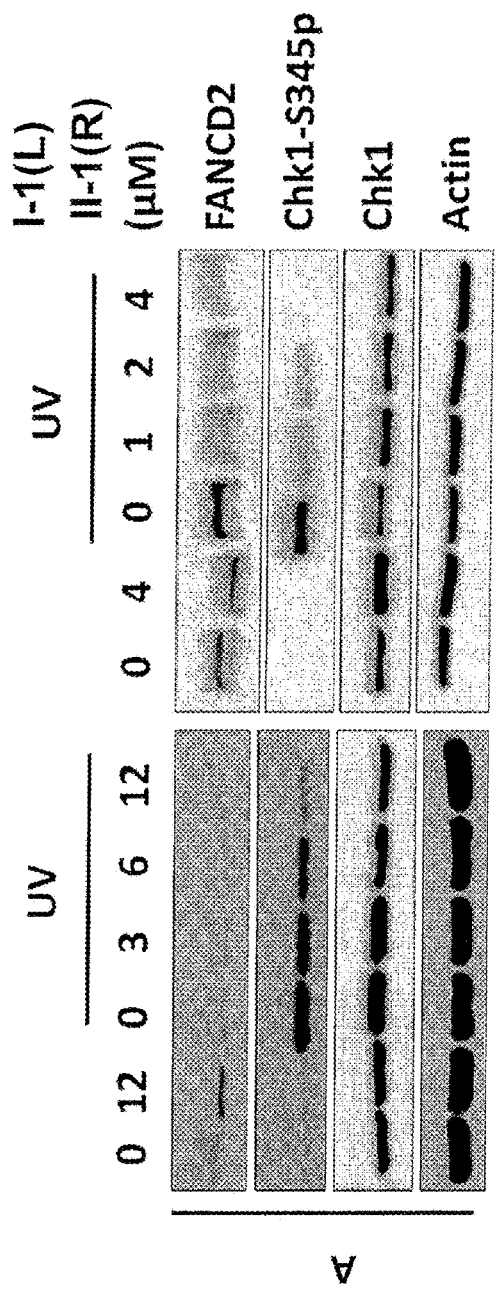
FIGS. 6(a)-6(b) show benzopyran-4-one derivatives inhibit UV-induced Chk1 phosphorylation.
Figure 6B:
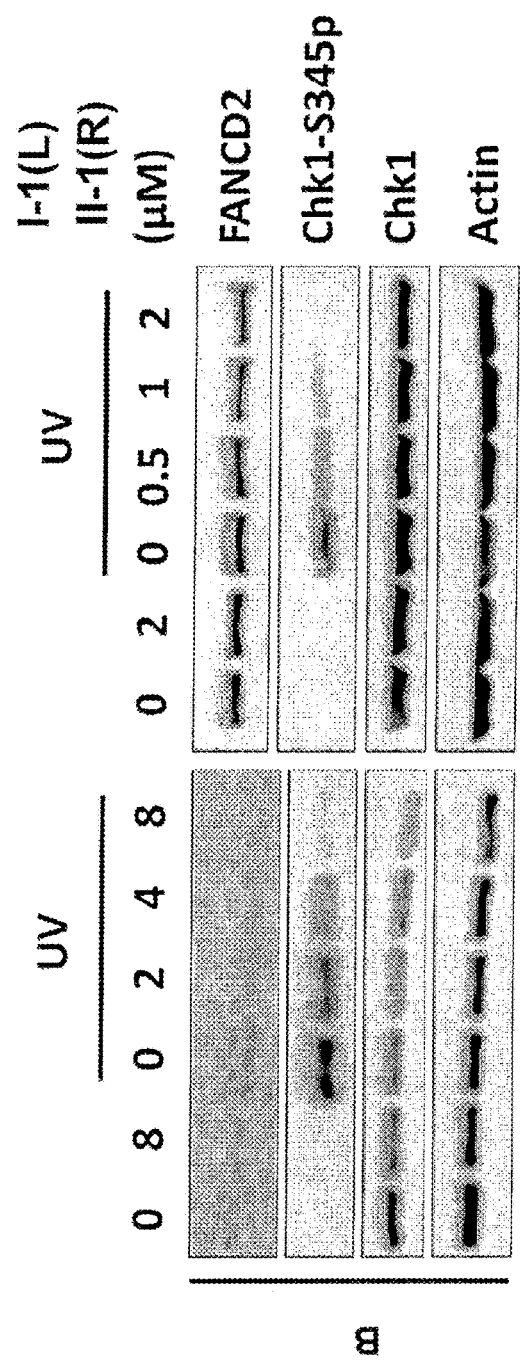
Figure 7:
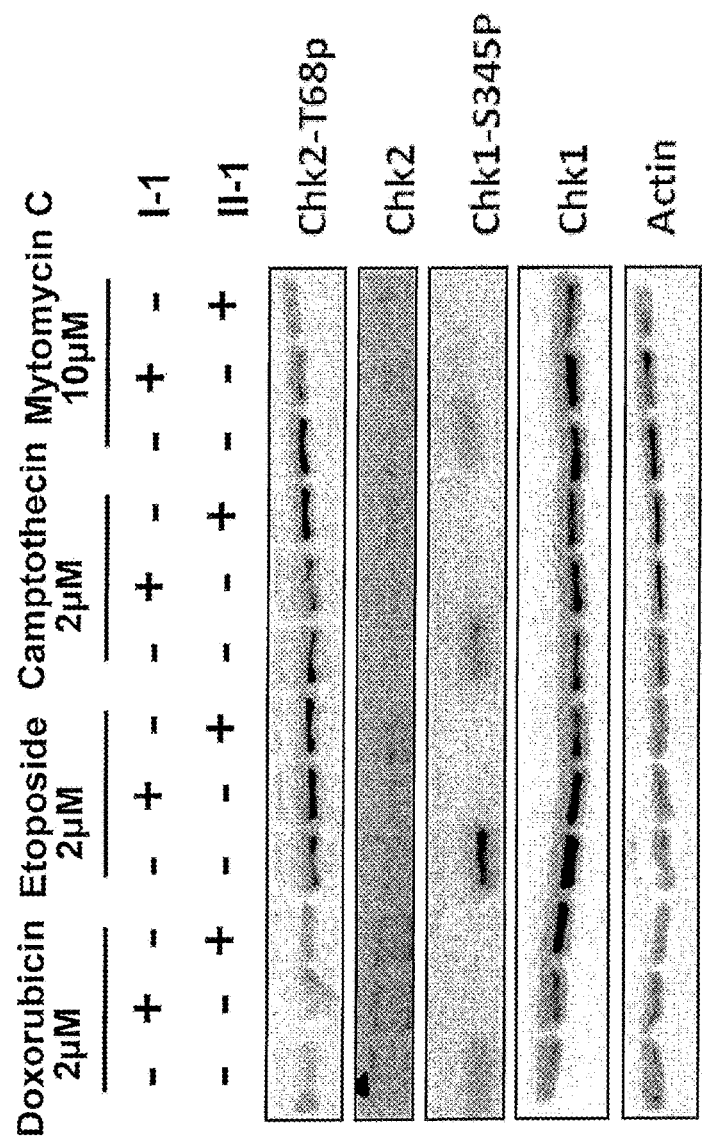
FIG. 7 shows benzopyran-4-one derivatives inhibit chemotherapeutic agents-induced Chk1 phosphorylation.

Understanding the mechanism by which the benzopyran-4-one derivatives compounds cause chromosomal breakages (FIG. 1) and other abnormalities might aid in identifying their targets. We hypothesized that genes with functions associated with DNA damage checkpoints and/or DNA repair might be targeted by benzopyran-4-one derivatives. To test this hypothesis, we assessed the effects of benzopyran-4-one derivatives on DDR induced by $H_2O_2$. Protoapigenone (I-1) was found to inhibit Chk1, but promote Chk2 phosphorylation in A594 cells treated with 0.1 mM $H_2O_2$ for 2 h; however, ATM autophosphorylation was not affected (FIG. 5(a)). Pretreatment of cells with okadaic acid (OA) (a phosphatase inhibitor) or MG132 (a proteasome inhibitor) could not reverse the Protoapigenone (I-1)-induced inhibition of Chk1 phosphorylation, indicating that the inhibition does not occur due to phosphatase activation or proteasome degradation by other regulatory factors (FIG. 5(b)). Further, we investigated other sources of DNA stimuli specific for ATR activation; our results demonstrate that UV-induced Chk1 phosphorylation was dose-dependently inhibited by benzopyran-4-one derivatives within different cells (FIGS. 6(a) and 6(b)). In response to DNA double-strand breaks (DSBs), FANCD2 is known to be monoubiquitinated on K561 (FANCD2-Ub) in an ATR-dependent manner to stimulate repair (Andreassen P R, et al. Genes Dev 2004). We showed that FANCD2-Ub was also inhibited by benzopyran-4-one derivatives (FIGS. 5(a), 6(a) and 6(b)); further, ATR inhibition by benzopyran-4-one derivatives was also observed in cells treated with currently prescribed chemotherapeutic agents (FIG. 7). Collectively, these findings indicate that benzopyran-4-one derivatives can modify ATR signaling after various types of DNA damage. Interestingly, compound II-1 was more potent than Protoapigenone (I-1) in inhibiting Chk1 phosphorylation and cytotoxicity (FIGS. 4, 6(a) and 6(b)).

We speculate that the replacement of 2 hydroxyl groups on Protoapigenone (I-1) with an additional benzene ring contributes positively to this ATR inhibition; however, the definite pharmacophores need to be further investigated when the ATR protein structure is resolved.

Target Specificity of Protoapigenone (I-1) and Compound II-1 for ATR-Mediated Signaling Inhibition.

Figure 8A:
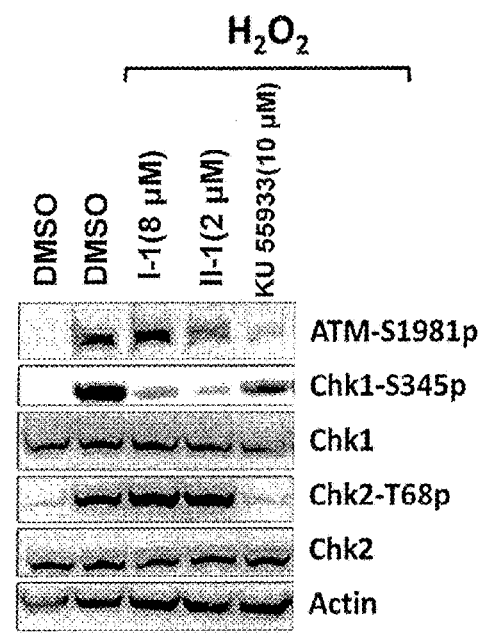
FIGS. 8(a)-8(b) show benzopyran-4-one derivatives inhibit ATR-dependent Chk1 phosphorylation.
Figure 8B:
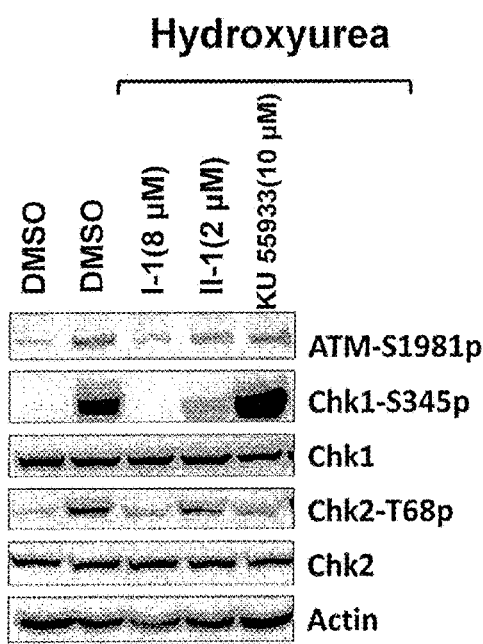
Figure 9:
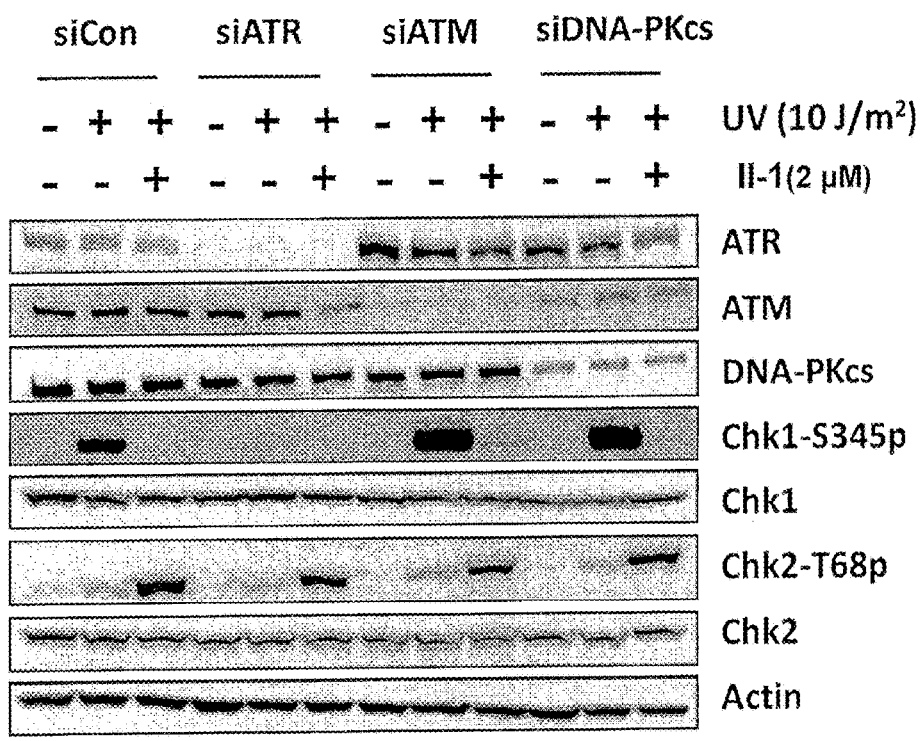
FIG. 9 shows the effect of compound II-1 on phosphorylation were assayed after UV irradiation on HEK293T cell, and this exhibited decreased expression of genes following the RNA interference treatment.
Figure 10A:
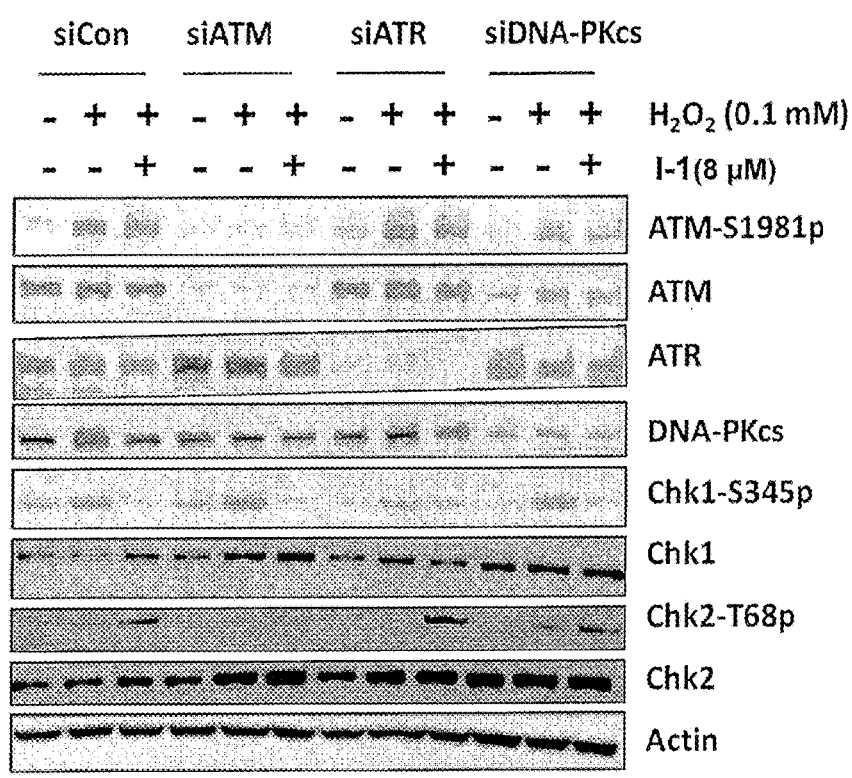
FIGS. 10(a)-10(c) show benzopyran-4-one derivatives inhibit UV- or $H_2O_2$-induced Chk1 phosphorylation
Figure 10B:
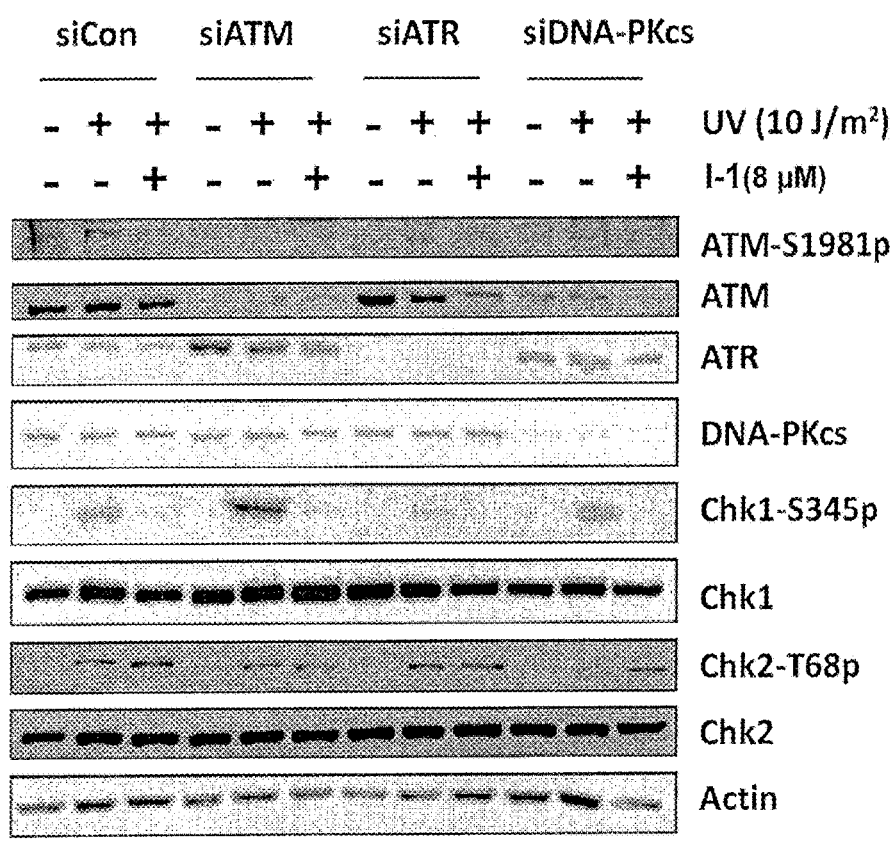
Figure 10C:
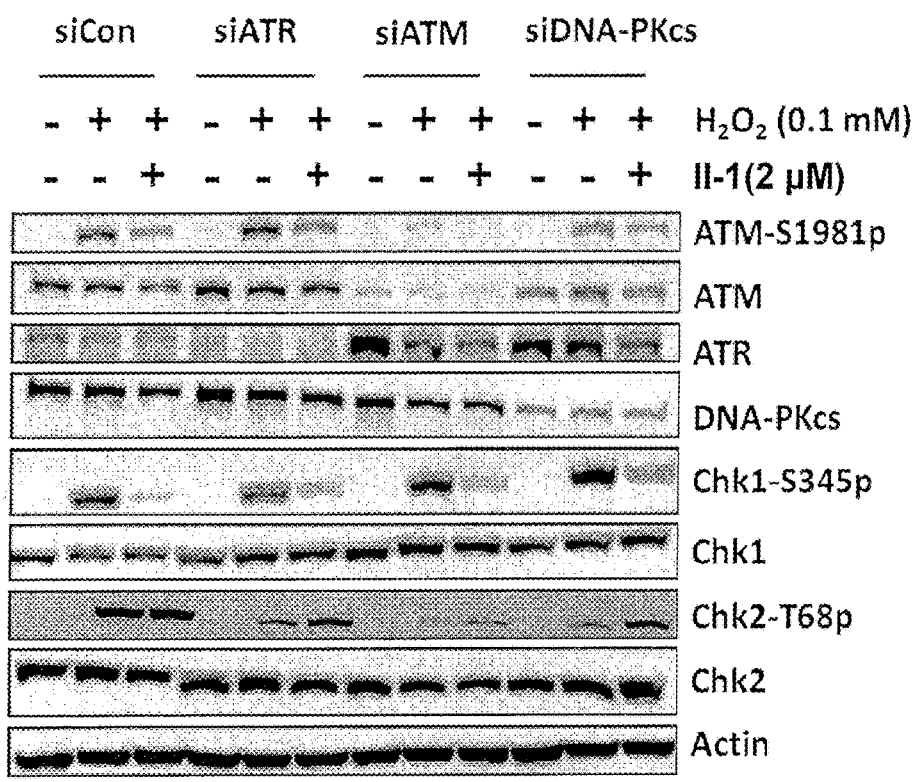

To elucidate the specificity of the benzopyran-4-one derivatives inhibition on ATR-mediated signaling, we compared the change between cells treated with benzopyran-4-one derivatives or the ATM-specific inhibitor KU55933 before the induction of DDR. After $H_2O_2$ damage, ATM is thought to be the principal responder, and KU55933 treatment strongly inhibited ATM-mediated Chk2 phosphorylation specifically, but its effect on ATR-mediated Chk1 phosphorylation was small (FIG. 8(a)). In contrast, after hydroxyurea (HU; a replication blocker) damage, ATR is thought to be the principal responder, and benzopyran-4-one derivatives treatment significantly inhibited Chk1 phosphorylation, but only slightly inhibited Chk2 phosphorylation (FIG. 8(b)).

Using these pharmacological methods, we demonstrated that the specificity of DDR inhibition between benzopyran-4-one derivatives and KU55933 was completely different. To strengthen the argument that benzopyran-4-one derivatives specifically inhibits ATR signaling, small inhibitory RNAs against ATM, ATR, and the catalytic subunit of DNA protein kinase (DNA-PKcs) were introduced into HEK293T cells before exposure to UV or $H_2O_2$.

Our results demonstrated that benzopyran-4-one derivatives completely inhibited UV-induced or $H_2O_2$-induced Chk1 phosphorylation in a manner similar to siRNA knockdown of ATR, but not ATM or DNA-PKcs (FIG. 9, FIGS. 10(a), 10(b) and 10(c)). The siRNAs against ATM and DNA-PKcs decreased the UV-induced or $H_2O_2$-induced Chk2 phosphorylation, which were not altered by the addition of Protoapigenone (I-1), but were increased by compound II-1 treatment. Interestingly, neither siRNA targeted to ATM or ATR nor DNA-PKcs affected the compound II-1-mediated increase in Chk2 phosphorylation. Since a high dose of compound II-1 itself slightly induces Chk2 activation (FIGS. 3(a) and 3(b)), the increased Chk2 phosphorylation was likely a synergistic effect due to DNA damage.

Figure 11:
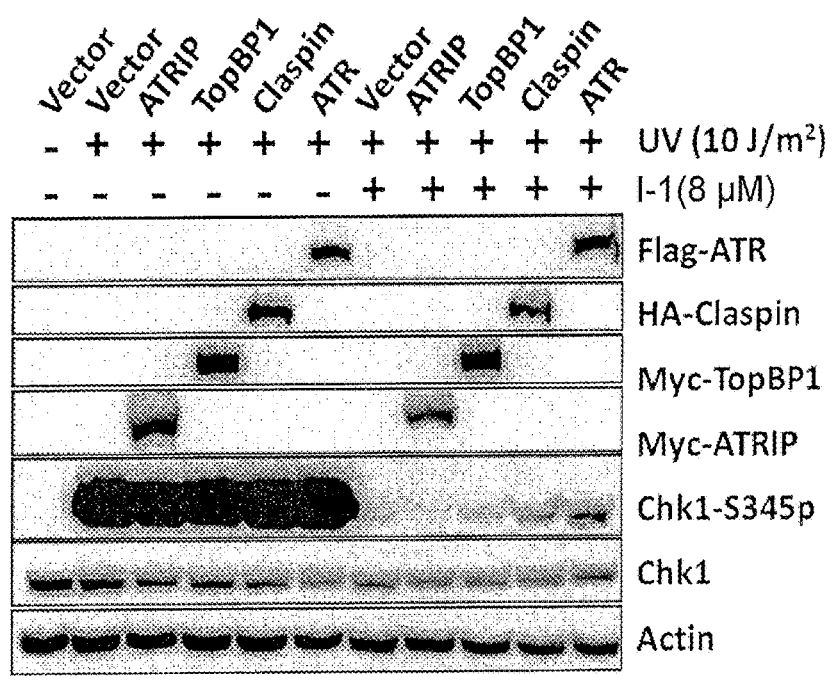
FIG. 11 illustrates immunoblots showing compound I-1 inhibit $H_2O_2$-induced Chk1 phosphorylation. Effects of compound I-1 on Chk1 phosphorylation were assayed 1 h after 10 J/m² UV irradiation on HEK293T cell overexpressing ATRIP, TopBP1, claspin, or ATR following delivery of tagged full-length cDNA constructs for 48 h.

To further identify the specific mediator that contributes to the effect of Protoapigenone (I-1) on the initiation of ATR kinase activation, we tested whether TopBp1, ATRIP, and claspin were involved, as they have been identified as mediators of ATR kinase activation (Lopez-Contreras A J, et al. DNA Repair (Amst) 2010). Our results demonstrated that overexpression of ATRIP or TopBP1 did not reverse the inhibitory effect of Protoapigenone (I-1) on Chk1 phosphorylation, whereas overexpression of claspin or ATR did (FIG. 11), suggesting that Protoapigenone (I-1) might affect the function of ATR or claspin contributes to ATR signaling inhibition.

Protoapigenone (I-1) and Compound II-1 Impair the Functions of DNA Damage Checkpoints and DNA Repair.

Figure 12A:
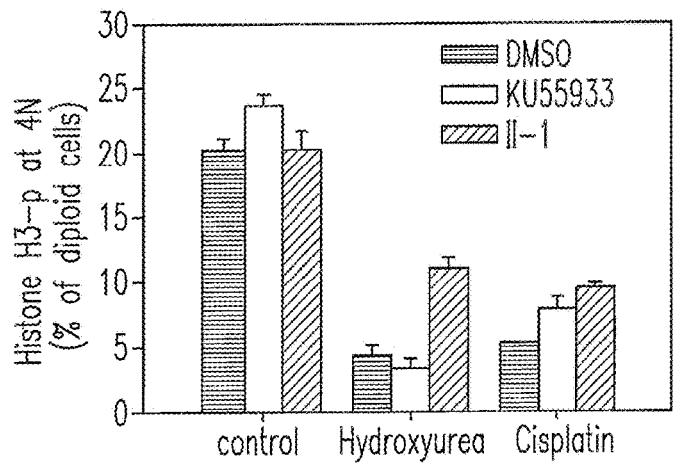
FIGS. 12(a)-12(b) show benzopyran-4-one derivatives inhibit DNA damage checkpoint and repair.

Previously, it has been demonstrated that S/M and G2/M checkpoints are activated by ATR in response to different types of DNA damage (Nghiem P, et al. Proc Natl Acad Sci USA 2001). Of these, the G2/M checkpoint involves ATM and ATR in collaboration, whereas the S/M checkpoint is mediated solely by ATR. To maintain genetic integrity, ATR can prevent premature mitotic entry in the event of incomplete DNA replication or unrepaired DNA damage. In order to evaluate the effect of benzopyran-4-one derivatives on these ATR-associated DNA damage checkpoints, we observed the effect of benzopyran-4-one derivatives on mitotic entry following hydroxyurea or cisplatin treatment. In MDA-MB-231 cells, hydroxyurea and cisplatin significantly decreased the number of mitotic cells, indicating that the S/M and G2/M checkpoints are intact in MDA-MB-231 cells (FIG. 12(a)).

TABLE 2

The percentage of mitotic cells

| | Control group | Compound | | |
|---|---|---|---|---|
| | | I-1 | II-1 | KU55933 |
| Control group | 20.28 ± 0.86 | 23.69 ± 0.94 | 12.05 ± 0.68 | 20.29 ± 1.48 |
| hydroxy-urea | 4.46 ± 0.67 | 3.40 ± 0.41 | 10.49 ± 1.17 | 11.19 ± 0.76 |
| cisplatin | 5.35 ± 0.07 | 7.99 ± 0.91 | 8.14 ± 0.99 | 9.70 ± 0.25 |

Benzopyran-4-one derivatives or KU55933 treatment increased the percentage of mitotic cells in cisplatin-treated cells, as the Table 2 suggesting that all of these compounds inhibited the damage-induced G2/M checkpoint. However, benzopyran-4-one derivatives, but not KU55933, significantly increased the HU-induced mitotic entry that is specific for the S/M checkpoint, indicating that benzopyran-4-one derivatives specifically impaired this distinctive checkpoint mediated solely by ATR (FIG. 12(a)).

ATR function is also linked to DNA repair via its coupled targets (Sorensen C S, et al. Nat Cell Biol 2005). To examine the effect of benzopyran-4-one derivatives treatment on DNA repair, we performed a homologous recombination repair (HRR) assay in HeLa cells.

TABLE 3

The percentage of GFP cell (DNA homologous recombination repair assay)

| | treatment | | GFP cell (%) |
|---|---|---|---|
| | Un-treatment group | 0.0 μM | 0.040 ± 0.0097 |
| chromosomal breaks generated by I-SceI endonuclease expression group | Un-treatment | 0.0 μM | 1.217 ± 0.0203 |
| | Compound I-1 | 2.0 μM | 0.807 ± 0.0403 |
| | | 4.0 μM | 0.213 ± 0.0105 |
| | Compound II-1 | 0.2 μM | 0.703 ± 0.0304 |
| | | 0.4 μM | 0.017 ± 0.0169 |

Figure 12B:
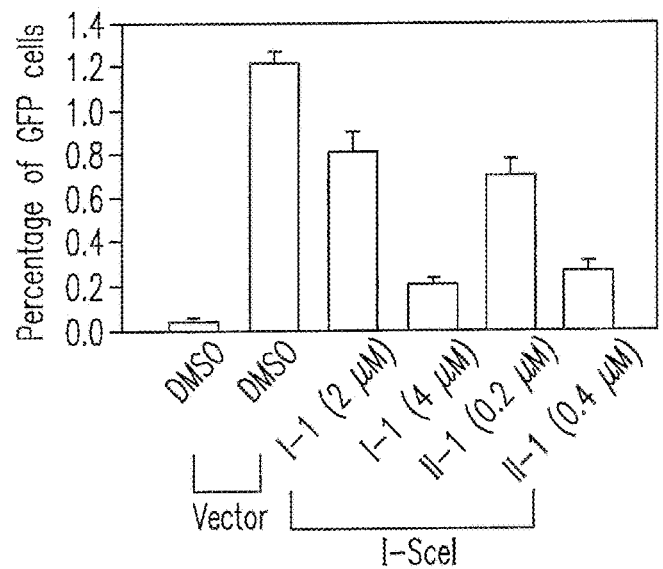
Figure 13:
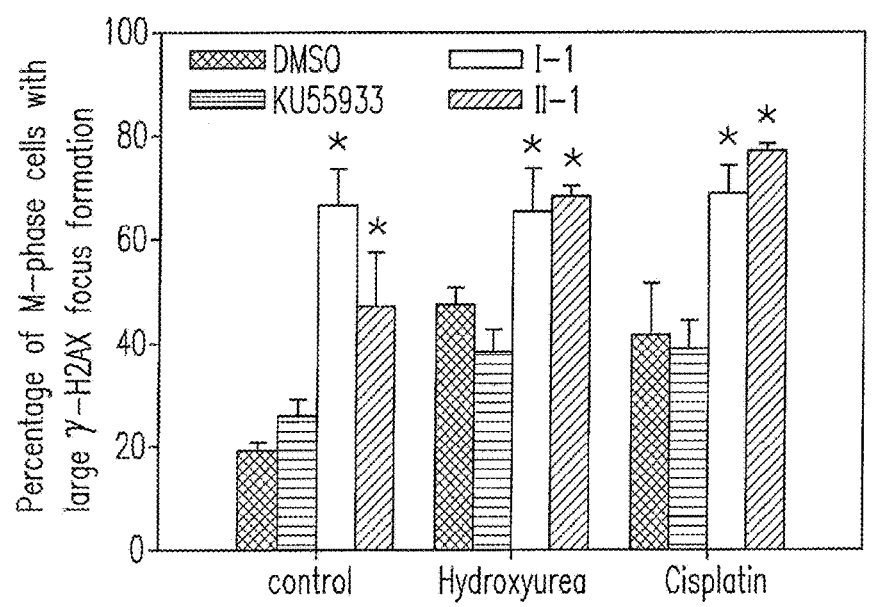
FIG. 13 illustrates the percentage of M-phase cells with γH2AX foucus formation.

Our result, as Table 3 demonstrated that chromosomal breaks normally repaired by HRR were dose-dependently inhibited by Protoapigenone (I-1) at low concentrations. Compound II-1 produced similar effects at doses that were 10-fold lower than that of Protoapigenone (I-1) (FIG. 12(b)). From these results, we assumed that the cells carrying unrepaired DNA would enter into mitosis following DNA damage. To verify this assumption, we analyzed the DNA-damage marker gamma-H2AX on mitotic cells using immunofluorescence staining. As expected, the numbers of large gamma-H2AX foci were increased upon addition of benzopyran-4-one derivatives in both unperturbed and perturbed mitotic cells (FIG. 13), suggesting that benzopyran-4-one derivatives increase DNA damage in mitotic cells. The chromosomes became flat and aggregated after benzopyran-4-one derivatives treatment, differing from the three-dimensional and hair-like appearance of normal chromosomes at metaphase.

Protoapigenone (I-1) and Compound II-1 Enhance Chemosensitivity.

Figure 14A:
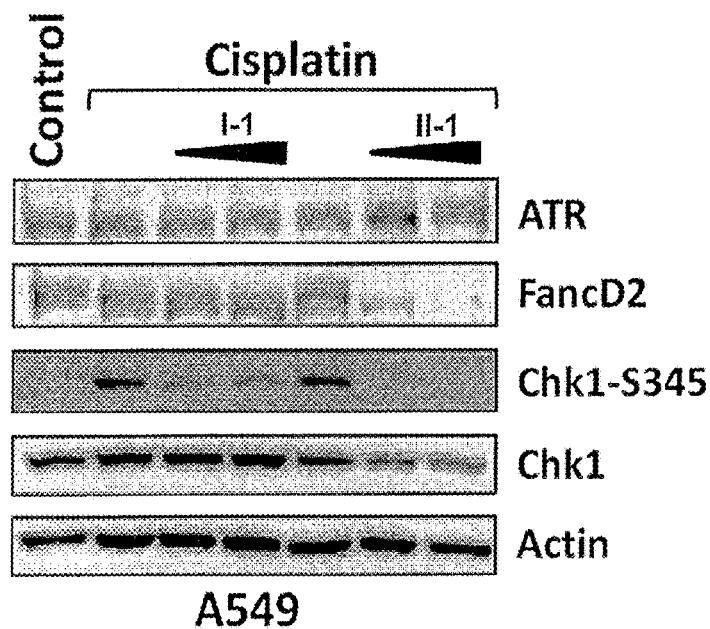
FIGS. 14(a)-14(c) show benzopyran-4-one derivatives inhibit cisplatin-induced Chk1 phosphorylation and FANCD2 monoubiquitination.
Figure 14B:
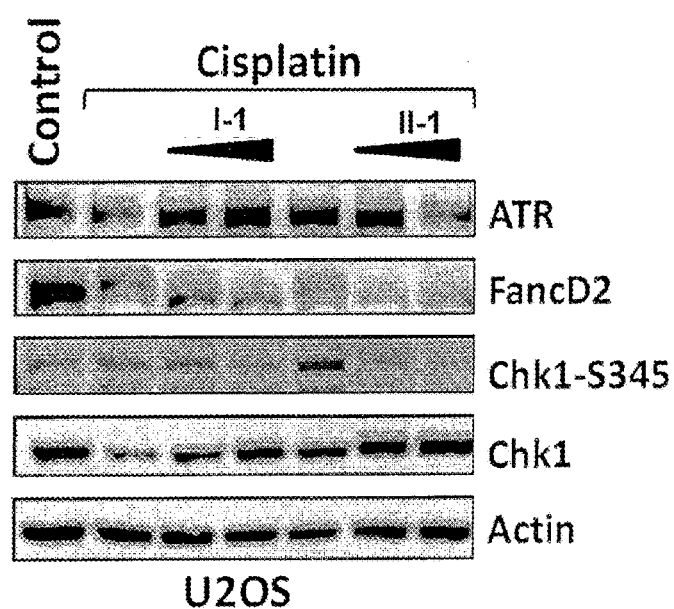
Figure 14C:
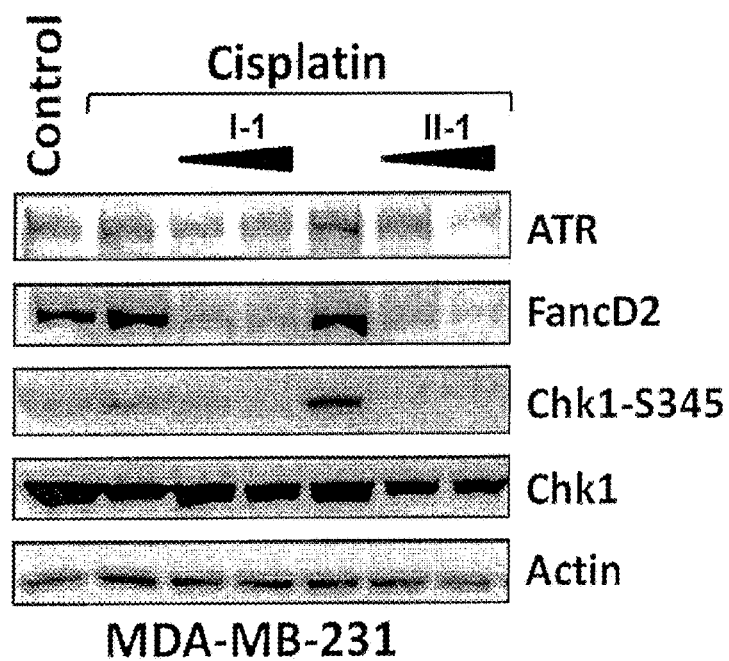
Figure 15A:
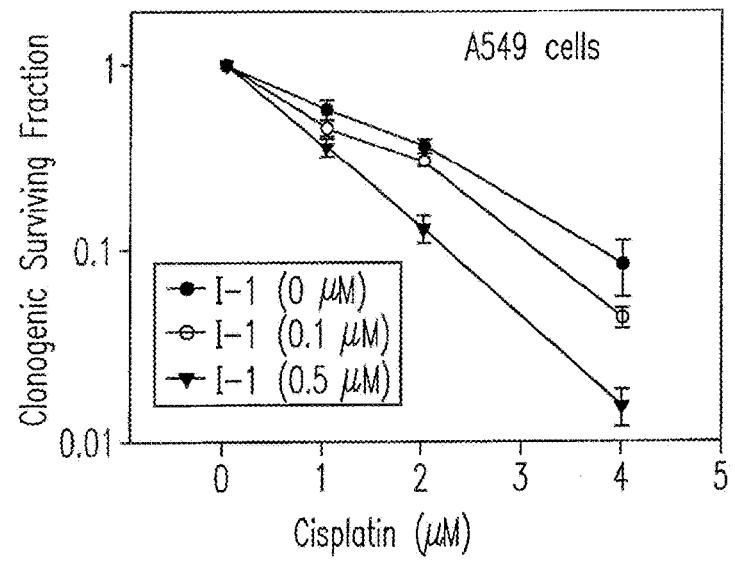
FIGS. 15(a)-15(b) show in vitro clonogenic survival for A549 cell.
Figure 15B:
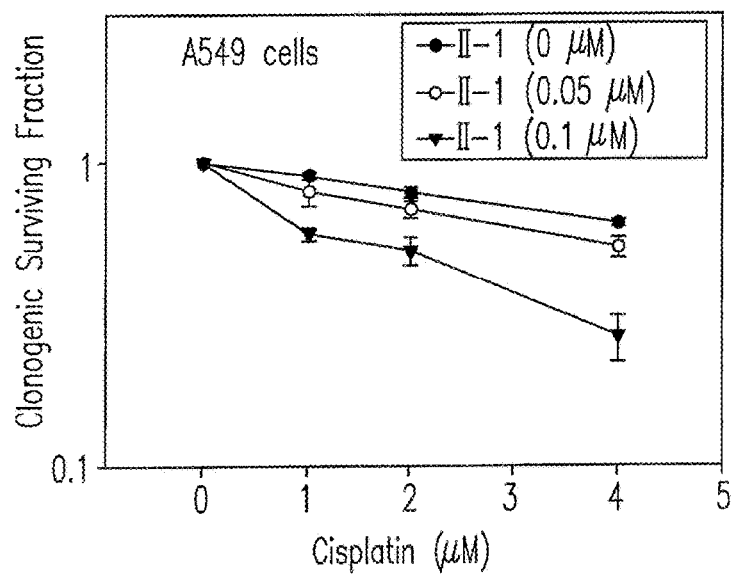
Figure 16A:
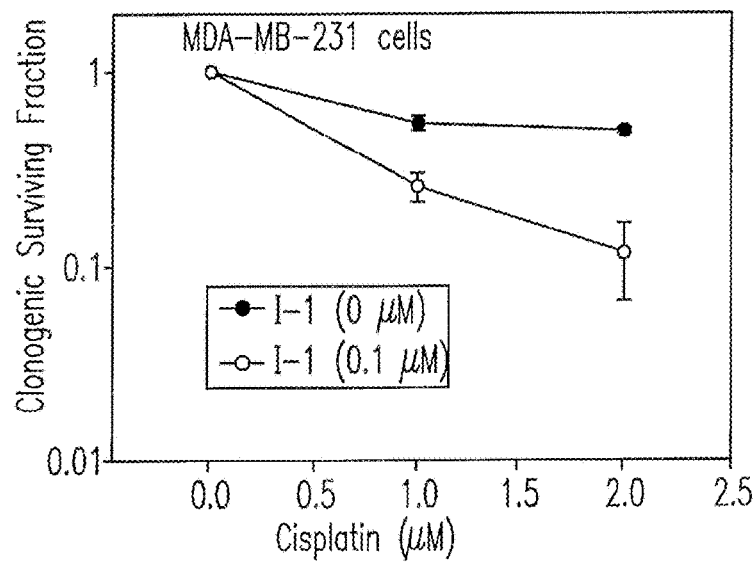
FIGS. 16(a)-16(b) show in vitro clonogenic survival for MDA-MB-231 cell.
Figure 16B:
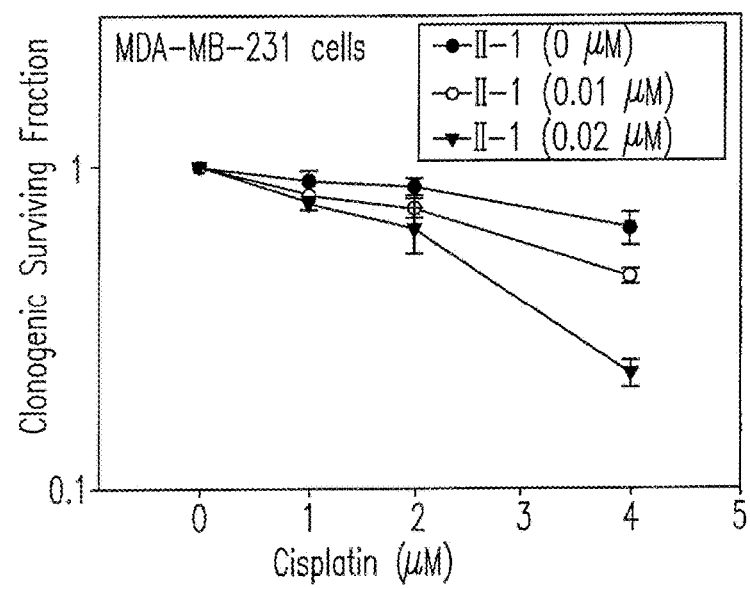
Figure 17A:
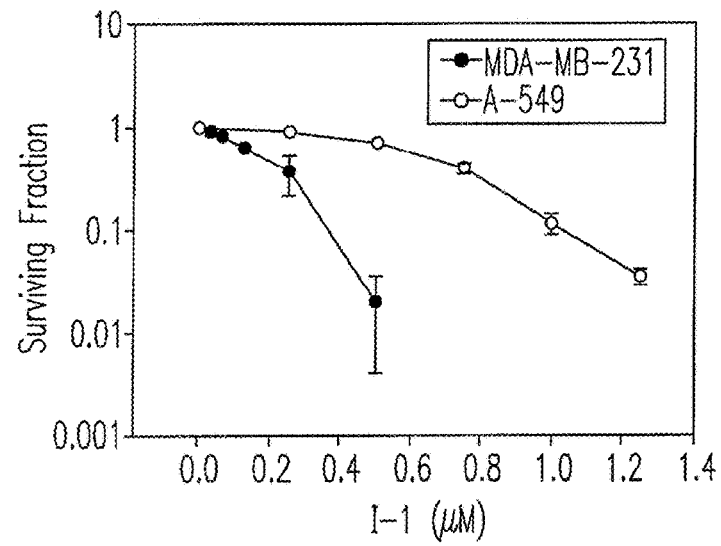
FIGS. 17(a)-17(b) show chemosensitization effect of benzopyran-4-one derivatives.
Figure 17B:
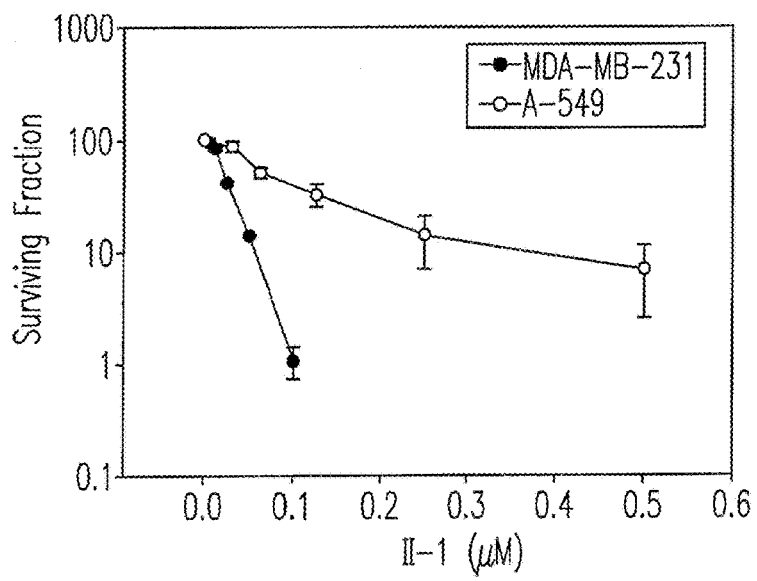
Figure 18:
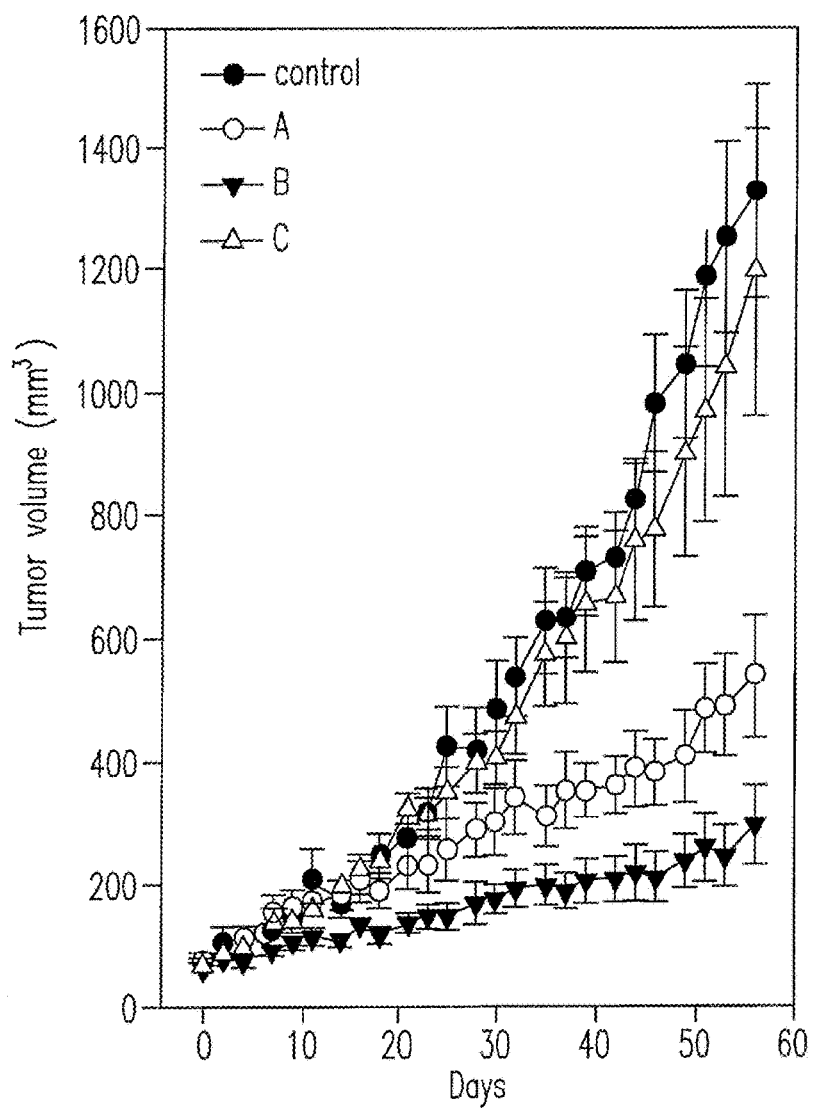
FIG. 18 shows in vivo xenograft tumor volume for MDA-MB-231 cell.
A—cisplatin 2 mg/kg
B—cisplatin+compound II-1 0.2 mg/kg
C—compound II-1 0.2 mg/kg
Figure 19A:
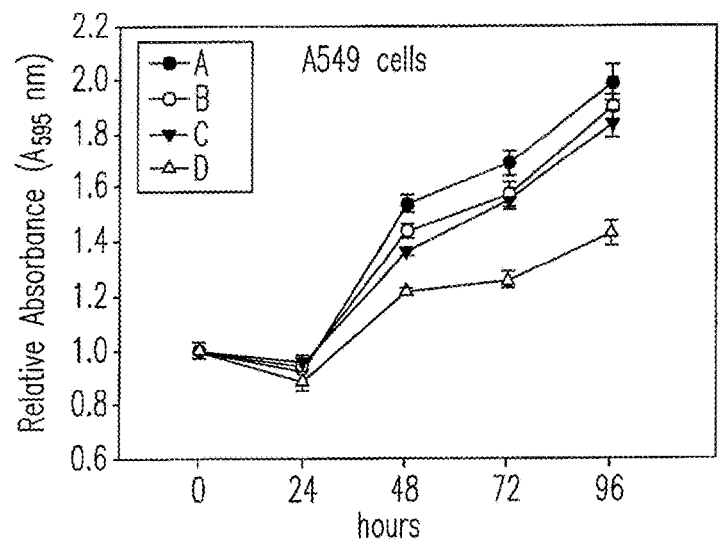
FIGS. 19(a)-19(b) show optical activity of benzopyran-4-one derivatives.
Figure 19B:
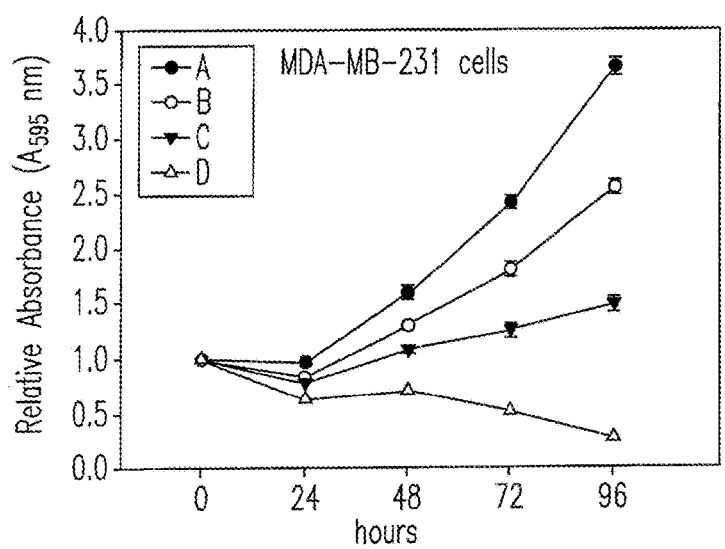
Figure 20A:
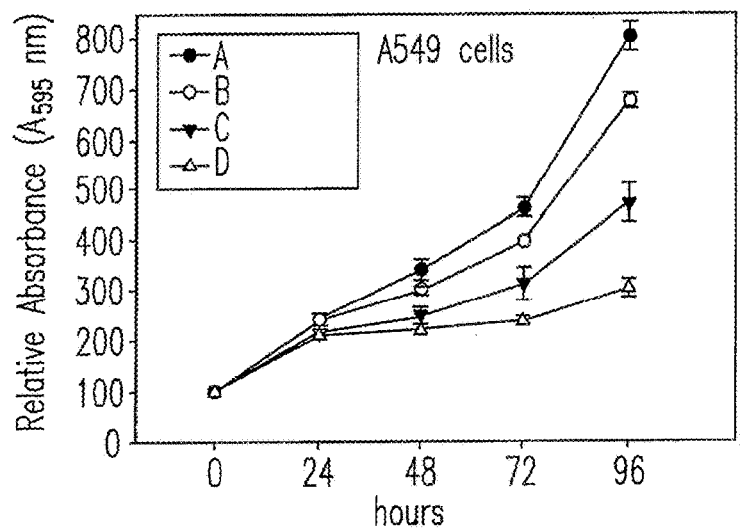
FIGS. 20(a)-20(b) show optical activity affected by benzopyran-4-one derivatives concentration.
Figure 20B:
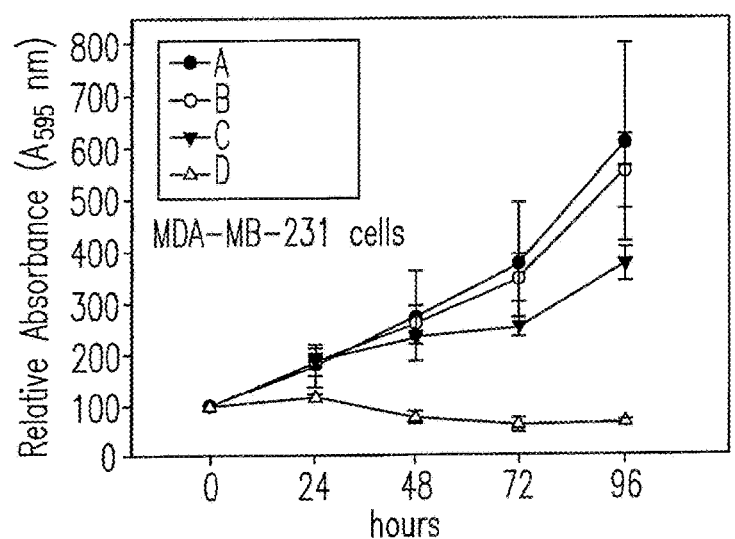

Inhibition of the checkpoint and repair mechanisms leads to chemosensitization in cancers. We questioned whether benzopyran-4-one derivatives could function as sensitizers for the chemotherapeutic drugs cisplatin that has been shown to induce ATR activation as well as FANCD2 monoubiquitination, which is the vital step for DNA crosslink repair (Chimomas D, et al. Mol Cancer Ther 2006). We found that benzopyran-4-one derivatives treatment decreased the cisplatin-induced Chk1 phosphorylation and FANCD2 monoubiquitination in A549, MDA-MB-231, and U2OS cells (FIGS. 14(a), 14(b) and 14(c)). Using the same doses, compound II-1 not only inhibits monoubiquitination of FANCD2 but also affects FANCD2 protein stability; this data emphasizes that compound II-1 has more potent inhibitory effects as compared to Protoapigenone (I-1). We further treated individual cells with cisplatin in combination with several varying doses of benzopyran-4-one derivatives, and counted survival colonies to determine their ability to survive after cisplatin-induced damage. Our results demonstrated that benzopyran-4-one derivatives effectively decreased the clonogenic survival in cisplatin-treated MDA-MB-231 and A549 cells in the nanomolar dose range (FIG. 15(a), 15(b), FIGS. 16(a) and 16(b)). To investigate the chemosensitization effect of low-dose benzopyran-4-one derivatives in vivo, we established a tumor xenograft in nude mice using human MDA-MB-231 tumor cells, which are considered to be more resistant to cisplatin and are also sensitive to treatment with benzopyran-4-one derivatives, at least as compared to A549 cells (FIG. 4, FIGS. 17(a) and 17(b)). When the mice were treated with 0.2 mg/kg compound II-1 in combination with 2 mg/kg cisplatin, the tumor inhibitory effect was greater than that of cisplatin treatment alone (FIG. 18). However, Protoapigenone (I-1) unexpectedly did not affect the cisplatin sensitivity of MDA-MB-231 tumors when a higher dose of 2 mg/kg was used in our experiments (data not shown). The pharmacokinetic data of Protoapigenone (I-1) and compound II-1 needs to be compared in future studies to determine the differences in the chemical effects of these 2 compounds in vitro and in vivo.

Figure 21A:
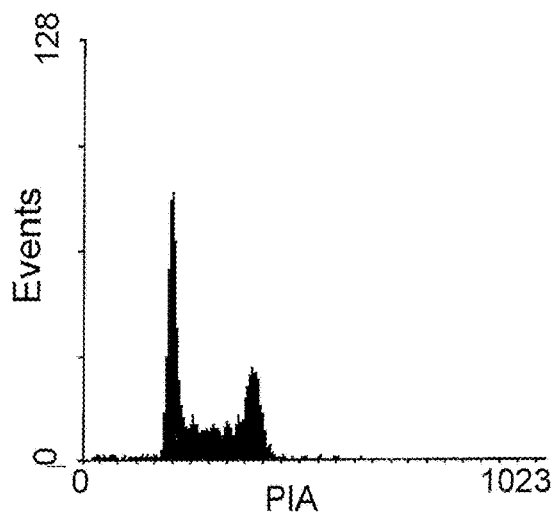
FIGS. 21(a)-21(b) show cell cycle progression rate.
Figure 21B:
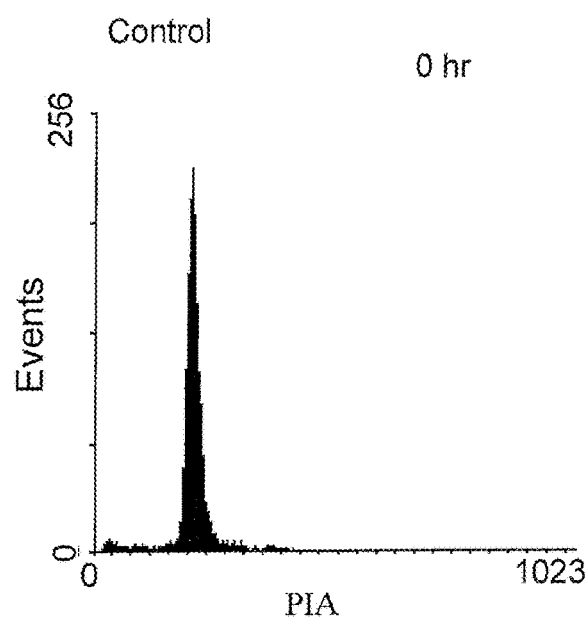
Figure 22A:
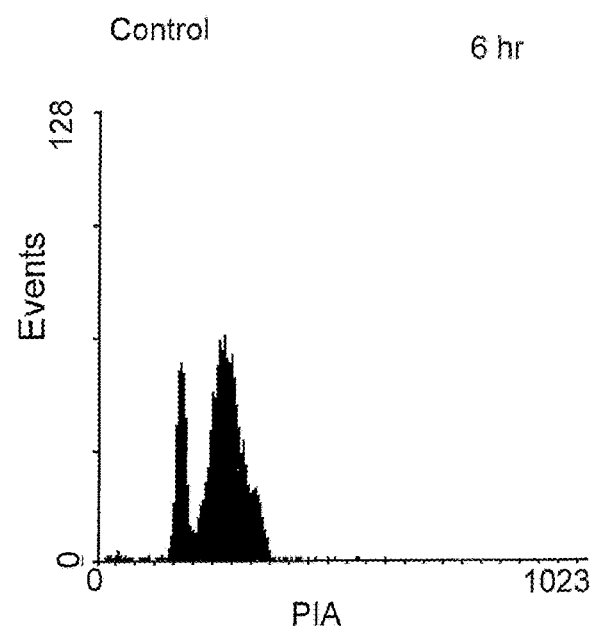
FIGS. 22(a)-22(c) show that rate of cell cycle progression were treated with benzopyran-4-one derivatives for 6 hrs.
Figure 22B:
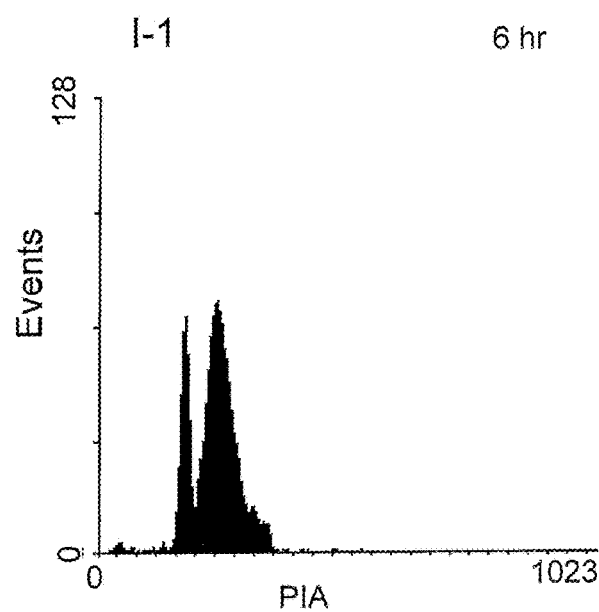
Figure 22C:
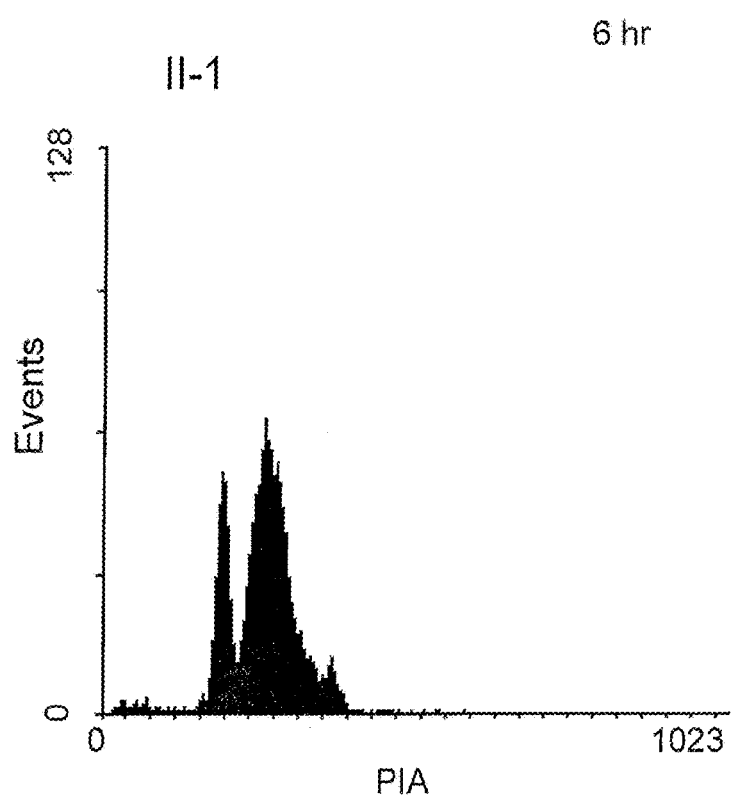
Figure 23A:
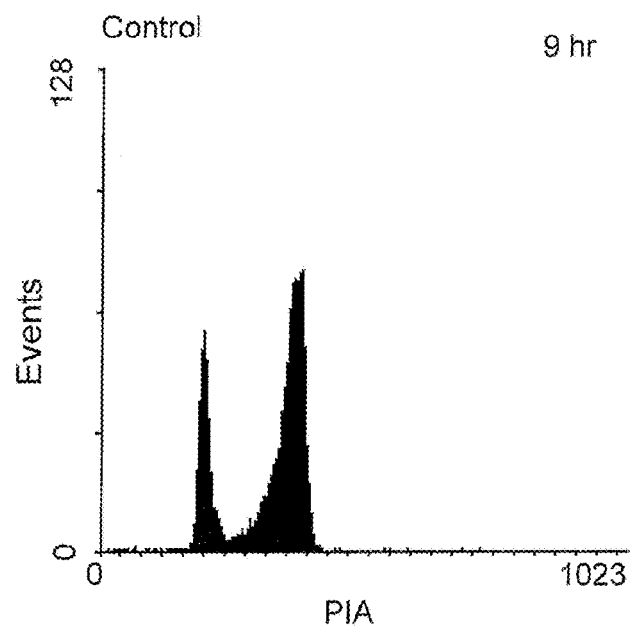
FIGS. 23(a)-23(c) show that rate of cell cycle progression were treated with benzopyran-4-one derivatives for 9 hrs.
Figure 23B:
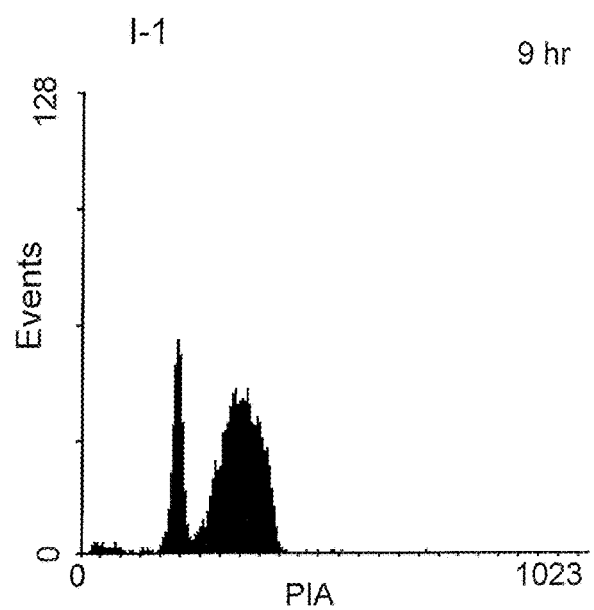
Figure 23C:
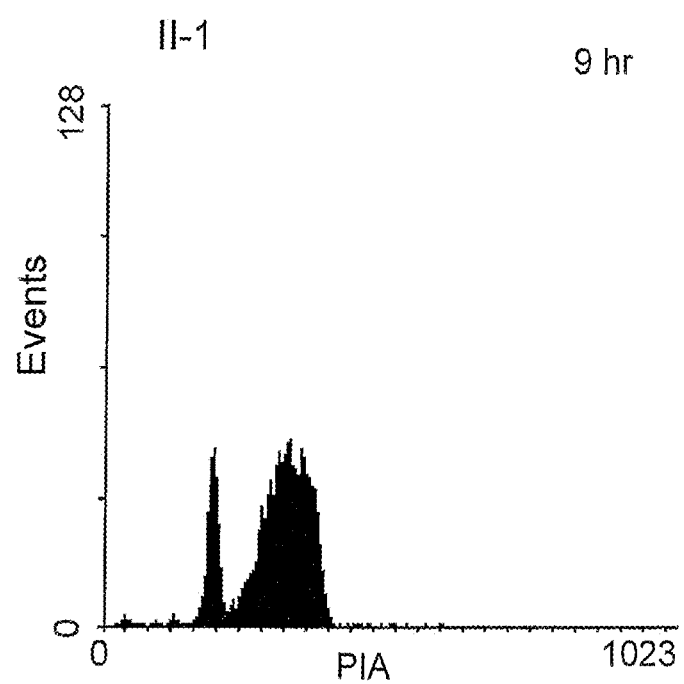

ATR are involved in DNA replication. Low doses of Protoapigenone (I-1) and compound II-1 significantly slowed cancer growth in a dose-dependent manner (FIGS. 19(a), 19(b), 20(a) and 20(b)), and caused S phase delay and inhibition of DNA synthesis (FIGS. 22(a), 22(b), 22(c), 23(a), 23(b) and 23(c)); these events are similar to previously reported characteristics of ATR defects. In the results of double-thymidine cell cycle synchronization assay, according to the Table 4 which sorted out from FIGS. 21-23, the unsynchronized cells (FIG. 21(a)) become synchronization by using this method, and 97% of cells were stopped at G1/S boundary after two cycles of thymidine blocks (FIG. 21(b)). Those synchronized cells released from thymidine blockade and allowed progress into S phase in presence or absence of protoapigenone (I-1) and compound II-1. Protoapigenone (I-1) (FIGS. 22(b) and 23(c)) and compound II-1 (FIGS. 22(c) and 23(c)) showed significantly reduce the percentage of G2/M cells at 9 hours of treatment in compared with control group (FIGS. 22(a) and 23(a)). So far, indicating that benzopyran-4-one derivatives with the ability to delay the S phase progression.

Figure 24A:
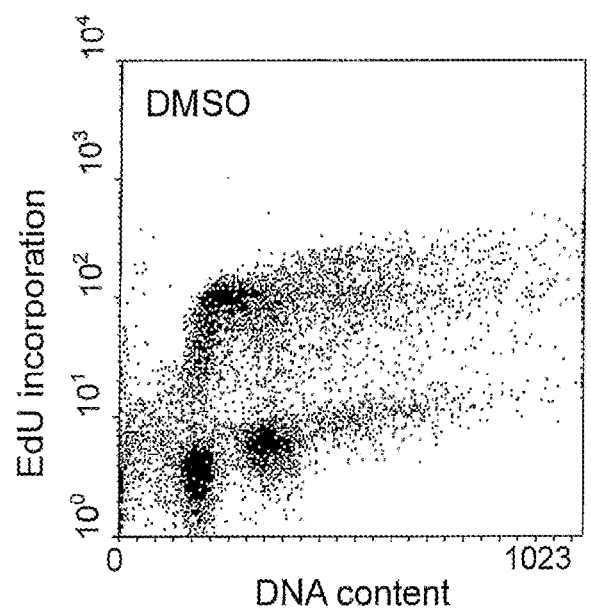
FIGS. 24(a)-24(e) show number of labeled DNA replication.
Figure 24B:
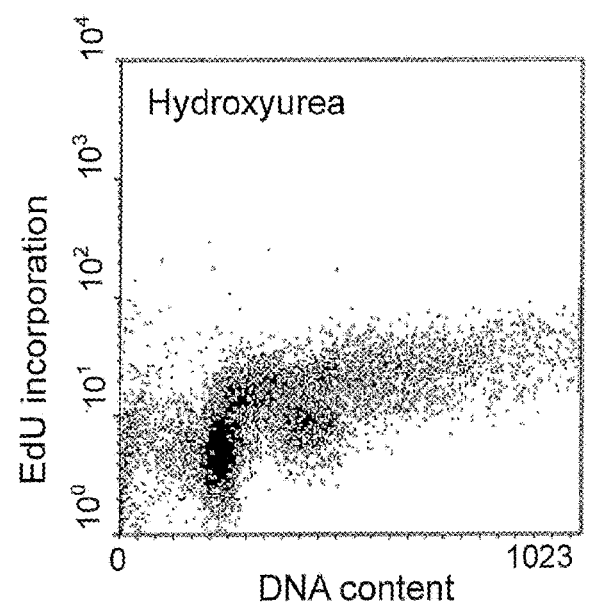
Figure 24C:
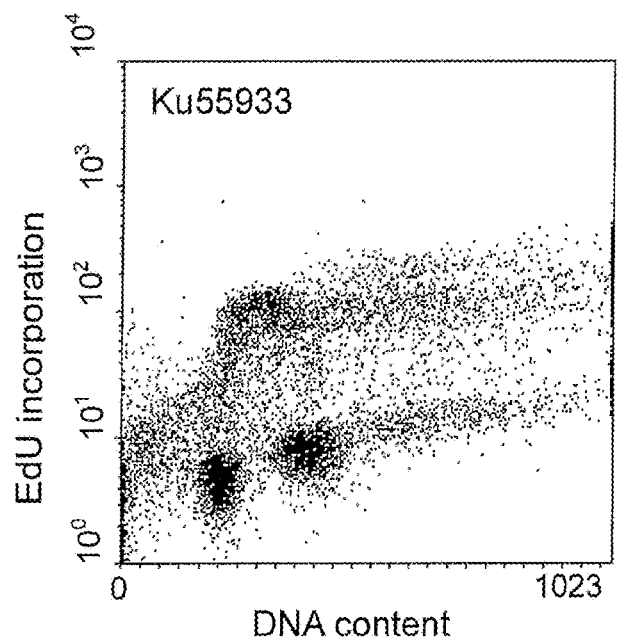
Figure 24D:
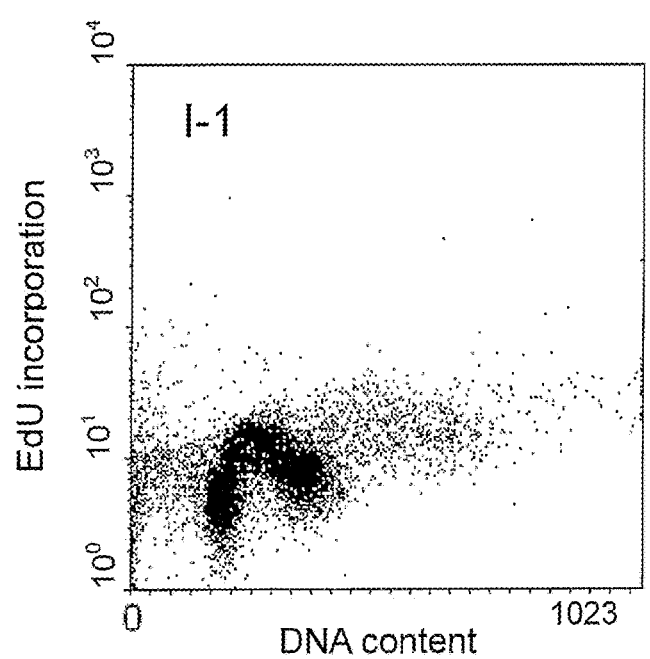
Figure 24E:
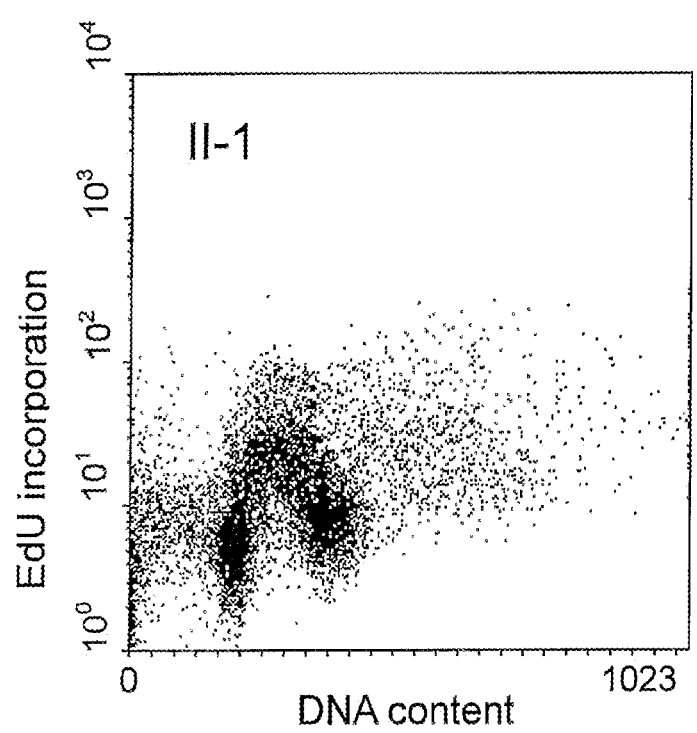
Figure 25:
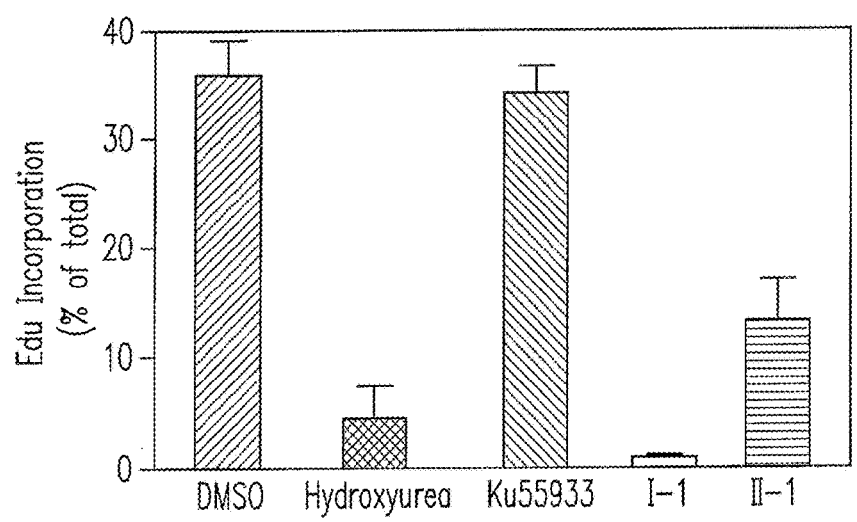
FIG. 25 illustrates the percentage of EdU incorporation.

Through EdU (5-ethynyl-2'-deoxyuridine) incorporation to measurement the capacity of DNA replication, 4 μM protoapigenone (I-1) (FIGS. 24(d)) and 0.4 μM compound II-1 (FIG. 24(e)) but not 10 μM ATM inhibitor KU55933 (FIG. 24 (c)) showed efficiently reduce the percentage of incorporation in compared with control group (FIG. 24(a)), indicating that DNA replication is inhibited (FIG. 25); these events are similar to the effect of a DNA replication blocker Hydroxyurea (HU) (FIG. 24(b)) and visualized that benzopyran-4-one derivatives with the ability to inhibit the DNA replication.

TABLE 4

| cell cycle | | | G1 | S | G2M |
|---|---|---|---|---|---|
| unsynchronized cells | | | 42.51% | 30.26% | 24.75% |
| initiation (0 hrs) | | Control | 70.95% | 24.00% | 1.29% |
| release synchronizeation | 6 hrs | Control | 18.29% | 75.63% | 0.63% |
| | | I-1 | 25.45% | 69.13% | 0.41% |
| | | II-1 | 21.72% | 72.01% | 4.59% |
| | 9 hrs | Control | 20.94% | 25.53% | 53.54% |
| | | I-1 | 21.41% | 60.89% | 16.46% |
| | | II-1 | 15.50% | 63.06% | 20.45% |

Materials and Methods
Antibodies

Primary antibodies of Chk1 (sc-8408), Chk2 (sc-17747), FANCD2 (SC-20022), phospho-ATM Ser1981 (sc-47739), and Myc (sc-40) were purchased from Santa Cruz. Phospho-histone H3 Ser10 (06-570) and H2AX Ser139 (05-636) antibodies were purchased from Millipore. Claspin (2880) and phospho-Chk1 Ser345 (2348), phospho-Chk2 Thr68 (2661), phospho-P53 Ser15 (9286), P38 MAPK Thr180/Tyr182 (9216), and MAPKAPK2 Thr334 (3007) were purchased from Cell Signaling. Actin (A2066), flag (F1804), and hemagglutinin (H9658) antibodies were purchased from Sigma-Aldrich. ATR (A300-137A), ATRIP (A300-095A), and TopBP1 (A300-111A) antibodies were purchased from Bethyl; and anti-ATM (GTX70103) antibodies were purchased from Gene Tex.

Cell Culture and Treatment.

MDA-MB-231 (breast adenocarcinoma; ATCC HTB-26, BCRC 60425) and A549 (lung adenocarcinoma; ATCC CCL-185, BCRC 60074) human cell lines were purchased from Bioresource Collection and Research Center (BCRC, Hsinchu, Taiwan), and were authenticated by American Type Culture Collection (ATCC, Manassas, Va.). U2OS (osteosarcoma), HeLa (cervical adenocarcinoma), and HEK 293T (embryonic kidney cells) human cell lines were provided by Dr. Sheau-Yann Shieh (Institute of Molecular Biology, Academia Sinica, Taipei, Taiwan). Cells were maintained in Dulbecco's modified Eagle's medium (DMEM, Sigma-Aldrich) supplemented with 10% fetal bovine serum (FBS) (Gibco). For DDR induction, freshly diluted $H_2O_2$ (Merck) was added to the culture medium 1 h before the cells were harvested. For UV irradiation treatment, the cells were irradiated for 10 $J/m^2$ by a cross-linker (UVP) 1 h prior to analysis. Protoapigenone (I-1) and compound II-1 were isolated and synthesized as described previously (15-17).

In Vitro Chemosensitization Assay.

To evaluate in vitro chemosensitization, cells were seeded in 6-well plates 1 d before the experiment at a density of 100-400 cells/well. The drugs were incubated with the cells for 6 h, after which the medium was replaced with fresh drug-free FBS-containing medium. The colonies became visible and were counted 7-10 d later using 0.1% crystal violet staining following image capture by a CCD camera (LAS-4000 mini; Fujifilm).

Flow Cytometry.

To evaluate the effect of DNA damage checkpoint activation on cell cycle distribution, the cells were harvested at indicated time points and fixed with methanol for at least 2 h. The DNA was then stained with a solution containing propidium iodide (PI) and RNase A (Sigma-Aldrich). Fluorescently labeled cells were subsequently analyzed by the flow cytometer (LSR II; BD Biosciences) with a suitable selection of excitation and emission wavelengths. The percentages of different fluorescent cell populations were analyzed using WinMDI Ver. 2.9 (The Scripps Research Institute).

DNA replication was measured using a Click-it EdU assay kit, which is based on incorporation of the thymidine analogue 5-ethynyl-2'-deoxyuridine (EdU) into DNA during replication (Invitrogen). Then, 10 µM EdU was added to the cell culture medium 30 min before the cells were harvested and fixed in 4% paraformaldehyde. After cycloaddition, EdU was detected with Alexa Fluor 647 using click reaction catalyzed by Cu (II), and the DNA content was stained by CellCycle 405-blue. To assay the mitotic entry, cells were treated with the indicated drugs and trapped in 70 nM nocodazole for 16 h, and antibodies against phospho-histone H3 Ser10 and PI were used to stain the mitotic cells and DNA content, respectively. An FITC Annexin V apoptosis detection kit was used to characterize the phenotype of cell death based on PI and Annexin V double staining (BD Pharmingen, San Diego, Calif.). Fluorescence-labeled cells were subsequently analyzed by the BD LSR II flow cytometer with a suitable selection of excitation and emission wavelengths. The percentages of different fluorescent cells were analyzed using WinMDI Ver. 2.9.

In Vitro Chromosome Aberration Test

In brief, $5\times10^5$ Chinese Hamster Ovary (CHO) cells were seeded in 60-mm dishes 1 d before the experiment. Protoapigenone (I-1)-induced structural chromosomal changes after 20 h were compared with that of the cells cultured in 2 µM mitomycin C. At 18 h after Protoapigenone (I-1), 0.1 µg/mL colchicine was added for 2 h, and metaphase cells were collected by shaking them off the dishes. Mitotic cells were treated with 0.5% KCl for 10 min and fixed with a 3:1 mixture of methanol: glacial acetic acid. The cells were then spread on slides for chromosome staining with 5% Giemsa solution. We then analyzed the chromosome structure of 200 well-spread metaphase cells (100 metaphase cells/experiment) under a 100× oil immersion objective.

Plasmids and siRNAs

The plasmids ATR, ATRIP, and claspin were kindly provided by Dr. X. Wu (The Scripps Research Institute, La Jolla, Calif.), and TopBP1 was provided by Dr. J. Chen (University of Texas MD Anderson Cancer Center, Houston, Tex.). The siRNA sequences of the target ATM (5'-AAGCGCCTGATTCGAGATCCT-3') [SEQ ID NO: 1], ATR (5'-CCTCCGTGATGTTGCTTGATT-3') [SEQ ID NO: 2], DNA-PKcs (5'-GATCGCACCTTACTCTGTTGA-3') [SEQ ID NO: 3], and the random sequence that served as the control (5'-AAGTCAATATGCGACTGATGG-3') [SEQ ID NO: 4] were synthesized by Sigma-Proligo (23,24). All transfections in HEK293T cells were performed by the calcium phosphate precipitation method.

Western Immunoblotting

Cell lysate preparations, gel electrophoresis, and immunoblotting were performed as previously described (23). The binding of primary antibodies were detected by horseradish peroxidase-coupled secondary antibodies (Jackson ImmunoResearch) followed by enhanced chemiluminescence (ECL) (Millipore). The images of non-saturated bands were captured using a luminescent image analyzer (LAS-4000 mini; Fujifilm). The antibodies used in this study are listed in supplementary materials.

DNA Homologous Recombination Repair Assay

DNA constructs of the recombination substrate pHPRT-DRGFP, in which the I-SceI site lies within 1 copy of 2 mutated tandem repeated GFP genes, and the I-SceI endonuclease expression vector pCBASceI, were originally constructed by Dr. M. Jasin (25). In brief, we generated a stable pHPRT-DRGFP construct in HeLa cells, and evaluated the chromosomal breaks generated by 1-SceI endonuclease expression. Six hours after pCBASceI was delivered into the cells, complete medium with or without Protoapigenone (I-1) or compound II-1 was replaced onto the cells. Forty-eight hours after delivery, the efficiency of chromosomal HRR was obtained as the percentage of GFP-positive cells, which was assessed by flow cytometry.

Human Xenograft Tumors in Nude Mice.

Human breast cancer MAD-MB-231 cells were harvested from the culture, resuspended in medium without serum at $1\times10^8$ cells/mL, and 0.1 mL of this suspension was subcutaneously injected into the right flank of female nude mice (BALB/cAnN-Foxn1nu/Crl Narl; purchased from the National Science Council Animal Center, Taiwan). Tumor-injected mice that successfully developed tumors that grew to approximately 50-100 mm³ in volume were randomly sorted into groups and used for the experiments. Control vehicle or 2 mg/kg of cisplatin with or without 0.2 mg/kg of compound II-1 was administered intraperitoneally every 4 d throughout the experiment.

Example 1: Preparation of the Composition in Tablet

Tablets are prepared using standard mixing and formation techniques as described in U.S. Pat. No. 5,358,941, to Bechard et al., issued Oct. 25, 1994, which is incorporated by reference herein in its entirety.

| | |
|---|---|
| Protoapigenone (I-1) | 100 mg |
| Lactose | qs |
| Corn starch | qs |

Proteins that are involved in DNA DNA-damage response pathways are positive for virus replication, including ATM, ATR, NBS, and FANCD2. We found that benzopyran-4-one derivative compounds can inhibit cells in response to oxidative stress, ultraviolet, and DNA-damaging chemotherapeutics induced signaling. Therefore, benzopyran-4-one derivative compounds may be able to inhibit virus infections by inhibiting the DNA damage signaling pathway.

To test the effects of anti-virus infection of benzopyran-4-one derivative compounds, a green fluorescent protein (GFP) expressing adenovirus to visualize adenovirus infection was used. To obtain the reporter virus, the GFP cDNA is amplified from pEGFP-N1 (Clontech, Accession: U55762.1) through a polymerase chain reaction with primers 5'-CACCATGGTGAGCAAGGGC-3' [SEQ ID NO: 5] and 5'-TACTTGTACAGCTCGTCCATG-3' [SEQ ID NO: 6], and then cloned into pENTR™/D-TOP vector (Invitrogen). The GFP cDNA was transferred to adenovirus vector pAd/CMV/V5-DEST™ through an in vitro recombination method using LR Clonase® II after the sequence was confirmed. We selected the ampicillin- and chloramphenicol-resistant clones to obtain the pAd-GFP. The pAd-GFP plasmid is then transfected into E1a and E1b expressing HEK293A cells to produce a crude GFP expression adenoviral stock (Ad-GFP). The adenovirus was amplified by infecting HEK293A cells. The adenoviral stock was titered and later used to infect the cells for the analysis.

In addition to the test of the benzopyran-4-one derivative compounds on the DNA virus infection, they were tested on the retrovirus using a GFP-expressing retrovirus to visualize the adenovirus infection. To obtain this virus, plasmids (obtained from the National RNAi Core Facility at Academia Sinica, Taiwan.) packaging plasmid pCMV-ΔR8.91 (containing gag, pol and rev genes), envelope plasmid pMD.G (VSV-G expressing plasmid), and TRC library plasmid pLKO_AS3.1w.eGFP.neo (GFP cDNA carrying plasmid) were co-transfected into a 6-well plate of the large T antigen expressing package cell line, HEK293T cells. 24 hours after transfection, BSA-containing media per plate was replaced with the original media to increase virus production, and the supernatant lentivirus was collected after an additional 16 hours. Afterward, the lentiviral stock (Lenti-GFP) was titered and used to infect the cells for analysis.

To observe the anti-virus effect of the benzopyran-4-one derivative compounds, Ad-GFP and Lenti-GFP at a low MOI of 0.5 were then applied to infect the HEK293A cells and HEK293T cells, respectively. The protocols for virus infection and compound treatment were shown in FIG. 26. In the prevention group, cells were treated by compounds of Compound I-1 at 0.2, 1, and 2 μM or Compound II-1 at 0.1, 0.5, 1 μM for 30 minutes before Ad-GFP and Lenti-GFP infection. In the treatment group, cells were treated by compounds of Compound I-1 at 0.2, 1, and 2 μM or Compound II-1 at 0.1, 0.5, and 1 μM for 2 hours after Ad-GFP and Lenti-GFP infection. After a total of 6 hours of compounds and virus treatments, cells were washed with Hank's buffered salt solution and a flash culture media was replaced.

24 hours after virus infection, the effect of the benzopyran-4-one derivative compounds on the antivirus infection was recorded by observing the GFP positive cells under an inverted fluorescence microscope. The mean fluorescence intensity by flow cytometry in each plate of cells was analyzed for quantification.

Figure 27A:
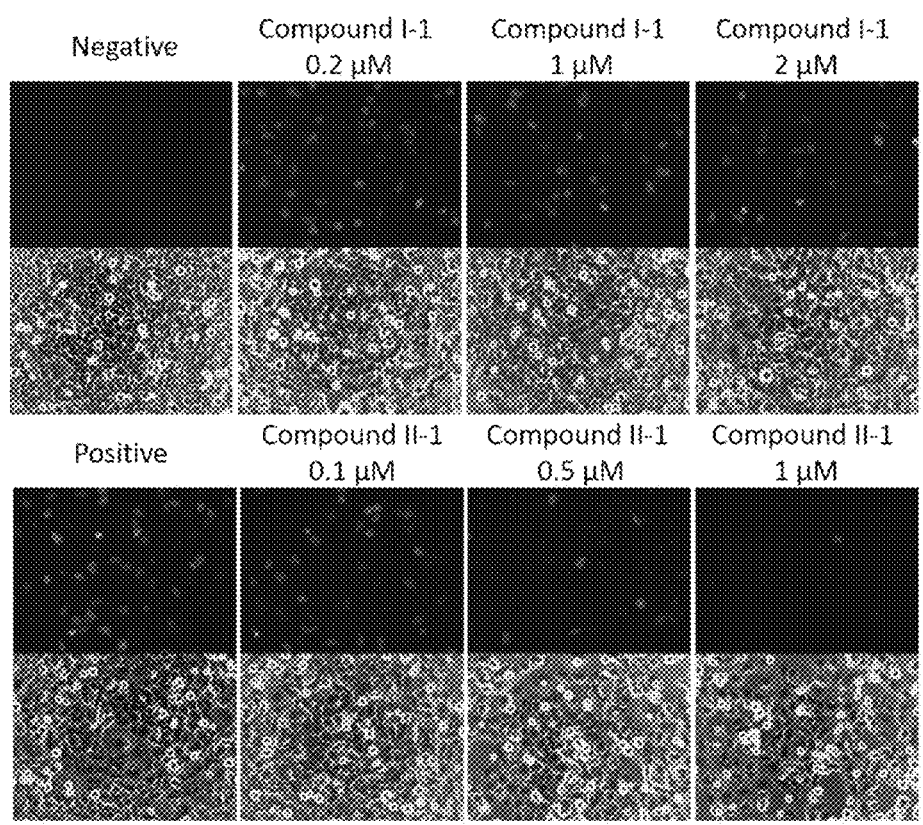
FIG. 27(a) illustrates the effects of pre-treatment of the compounds on the number of GFP cells.
Figure 27B:
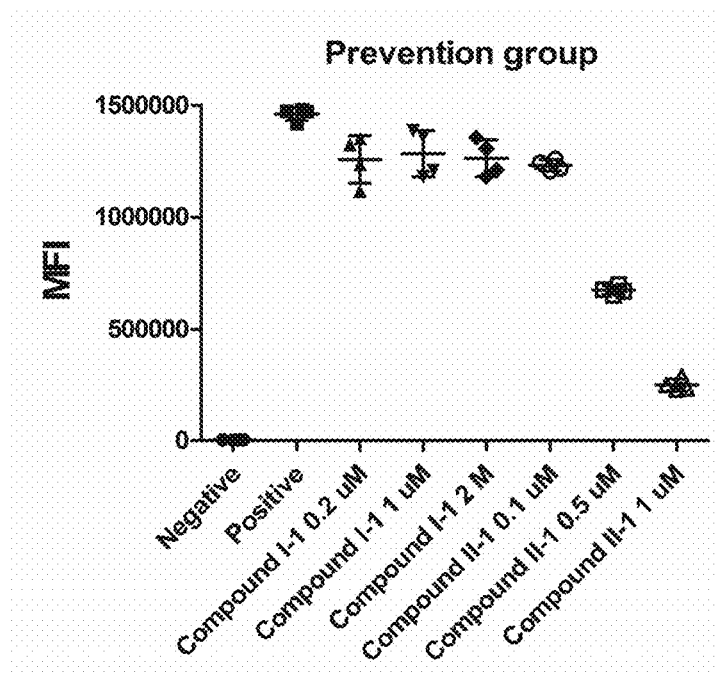
FIG. 27(b) illustrates the effects of pre-treatment of the compounds on the mean fluorescence intensity (MFI) of the GFP protein in Ad-GFP-infected cells.
Figure 27C:
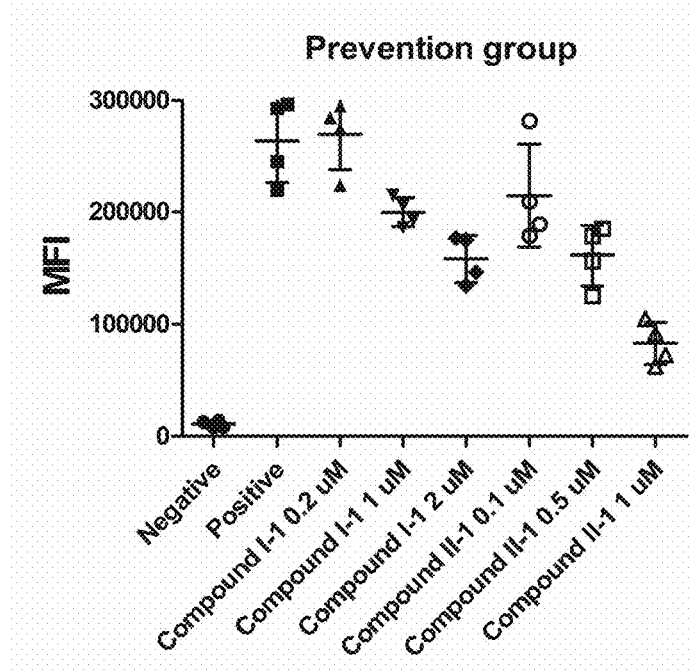
FIG. 27(c) illustrates the effects of pre-treatment of the compounds on the MFI of the GFP protein in Lenti-GFP-infected cells.

According to the results, pre-treatment of 0.1-1 μM of Compound II-1 decreased the number of GFP cells (FIG. 27(a)) significantly with a dose-dependent effect, as well as the mean fluorescence intensity (MFI) of GFP protein (FIG. 27(b)) in Ad-GFP-infected cells. Pre-treatment of Compound I-1 for 0.2-2 μM did not prevent the Ad-GFP infection. These results indicate that Compound II-1 is more potent in prevention of adenovirus infection than Compound I-1. Pre-treatment of 0.2-2 μM of Compound I-1 or 0.1-1 μM of Compound II-1 significantly decreased the MFI of GFP protein (FIG. 27(c)) in Lenti-GFP-infected cells with a dose-dependent effect. These results indicate that the benzopyran-4-one derivative compounds prevent the retrovirus infection. Compound II-1 is more potent to prevent retrovirus infection than Compound I-1.

Figure 28A:
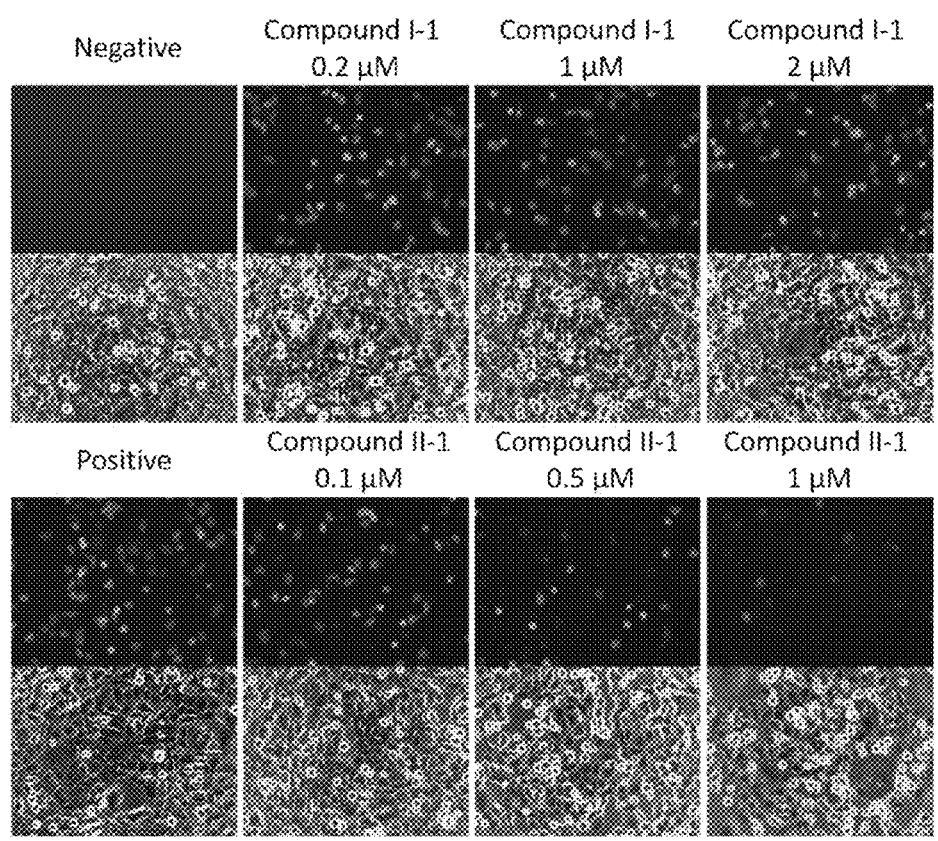
FIG. 28(a) illustrates the effects of post-treatment of the compounds on the number of GFP cells.
Figure 28B:
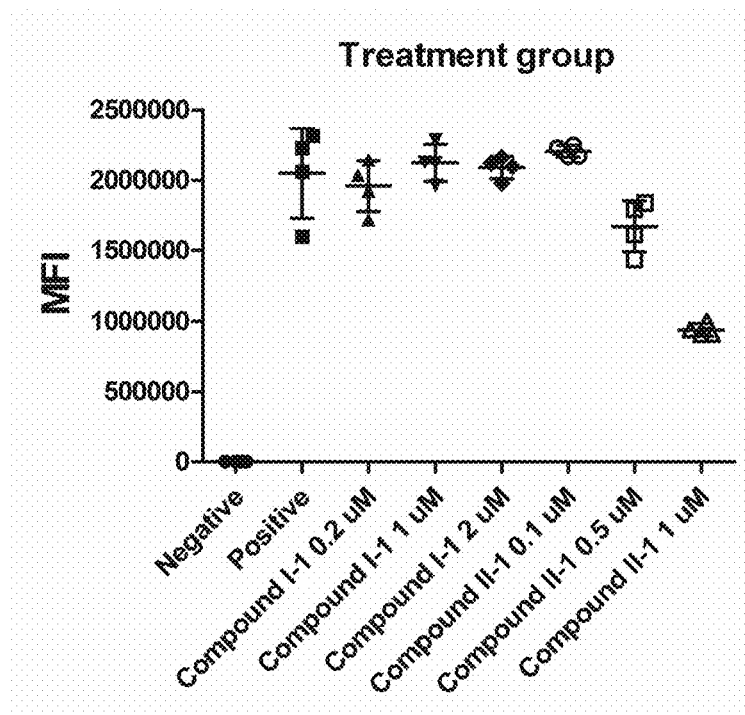
FIG. 28(b) illustrates the effects of post-treatment of the compounds on the MFI of the GFP protein in Ad-GFP-infected cells.
Figure 28C:
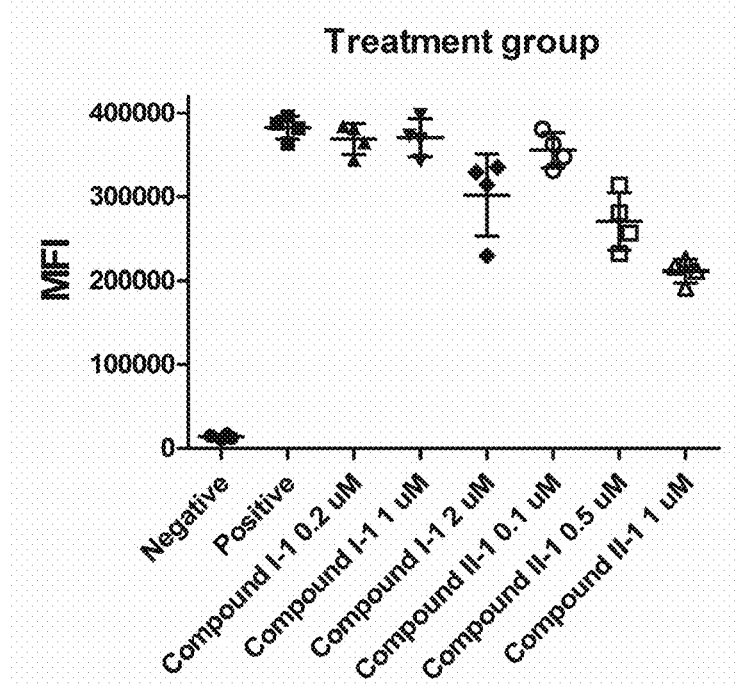
FIG. 28(c) illustrates the effects of post-treatment of the compounds on the MFI of the GFP protein in Lenti-GFP-infected cells.

Post-treatment of 0.1-1 μM of Compound II-1 after 2 hours of Ad-GFP virus infection decreased the number of GFP cells significantly with a dose-dependent effect (FIG. 28(a)), as well as the MFI of GFP protein (FIG. 28(b)) in Ad-GFP-infected cells. Treatment with Compound I-1 for 0.2-2 μM did not inhibit the Ad-GFP infection. These results indicate that Compound II-1 is more potent in treating adenovirus infection than Compound I-1. Post-treatment of 0.1-1 μM of Compound II-1 after 2 hours of Lenti-GFP infection significantly decreased the MFI of GFP protein in Lenti-GFP-infected cells with a dose-dependent effect. Treatment with Compound I-1 2 μM also showed an inhibition effect (FIG. 28(c)). These results indicate that the benzopyran-4-one derivative compounds are effective in treating retrovirus infection. Compound II-1 is more potent in treating retrovirus infection than Compound I-1.

Figure 26:
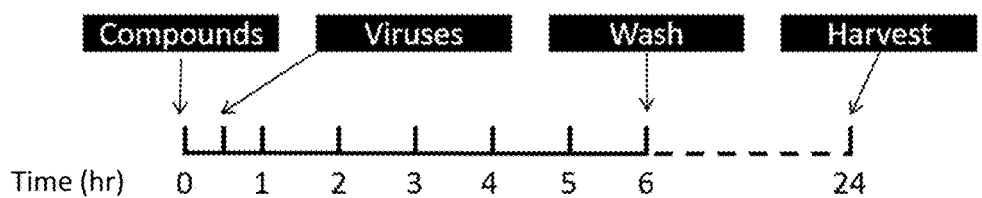
FIG. 26 illustrates the treatment protocol for virus infection and compound treatment.
Figure 26:
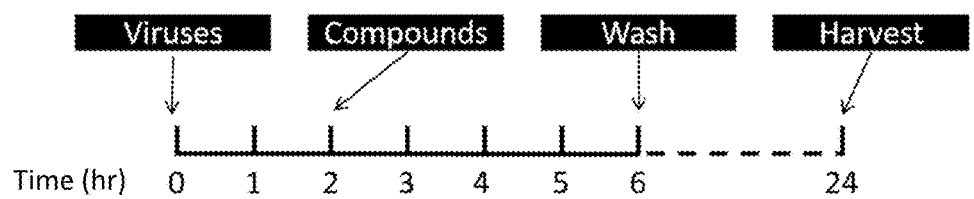

Based on the treatment protocol shown in FIG. 26, pre-treatment of benzopyran-4-one derivative compounds was more efficient than post-treatment. We infer that benzopyran-4-one derivative compounds affect virus infection in multiple steps. Moreover, the inhibition patterns of benzopyran-4-one derivative compounds in Ad-GFP and Lenti-GFP are quite similar, indicating that the mechanisms of these compounds for DNA virus and retrovirus infections are similar.

Ideally, the Ad-GFP virus is replicated within HEK293A cells. To test the effect of benzopyran-4-one derivative compounds on Ad-GFP virus replication, the same virus infection and compound treatment are performed as shown in FIG. 26. At the end of a 24-hour experiment, we collected the Ad-GFP virus from each well of Ad-GFP infected HEK293A using two freeze-thaw cycles and then collected the supernatants. An equal amount of supernatants from each well were then infected with the HEK293A cells, which were newly-prepared 1 day before infection in a 96-well plate at a density of $5 \times 10^4$ per well. Finally, the GFP cell images were obtained using the inverted fluorescence microscope and quantified by analyzing the MFI using flow cytometry for each well of cells.

Figure 29A:
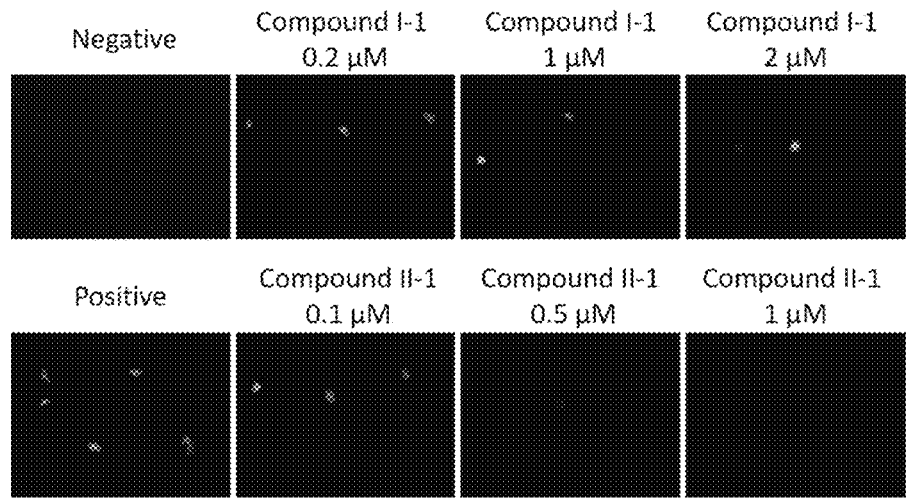
FIG. 29(a) illustrates the effects of pre-treatment of the compounds on the number of GFP cells.
Figure 29B:
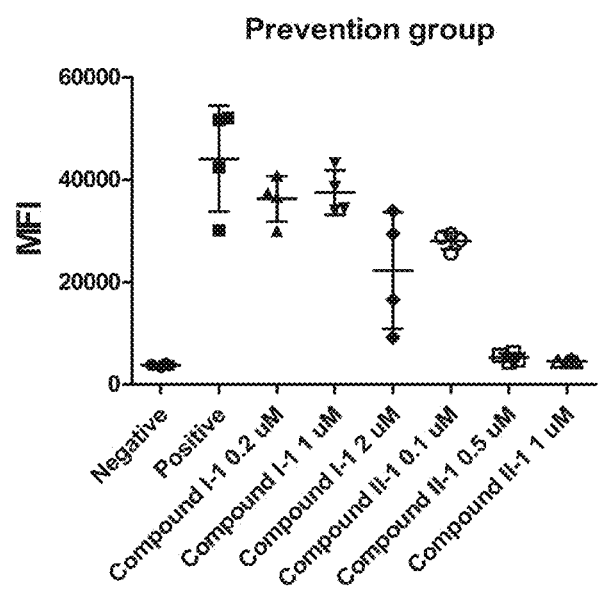
FIG. 29(b) illustrates the effects of pre-treatment of the compounds on the MFI of the GFP protein in Ad-GFP-infected cells.
Figure 29C:
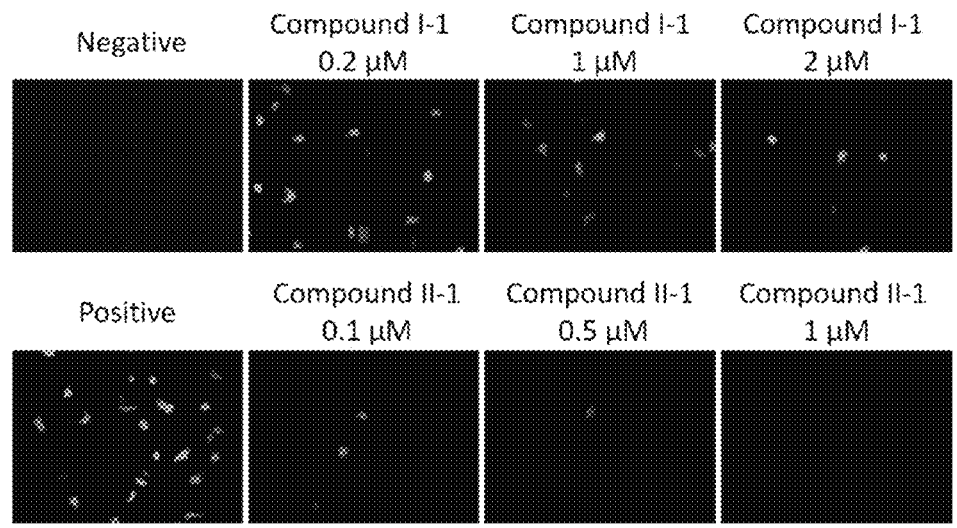
FIG. 29(c) illustrates the effects of post-treatment of the compounds on the number of GFP cells.
Figure 29D:
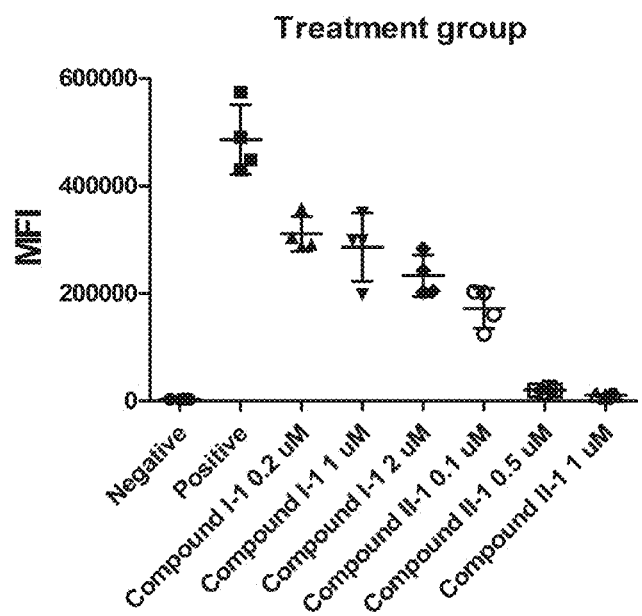
FIG. 29(d) illustrates the effects of the post-treatment of the compounds on the MFI of the GFP protein.

24 hours after isolating the Ad-GFP virus infected with the new prepared HEK293A cells, we found that the pre-treatment with Compound I-1 or Compound II-1 significantly decreased the number of GFP cells with a dose-dependent effect (FIG. 29(a)) as well as the MFI of GFP protein (FIG. 29(b)). The inhibition of virus infection including virus attaching to or entering the cells, may account for the inhibition of virus replication with Compound II-1 due to the significant inhibition of virus infection (FIG. 27). However, Compound I-1 significantly inhibited the virus replication in cells, proving that benzopyran-4-one derivative compounds prevent adenovirus replication since the same dose of Compound I-1 did not significantly inhibit the Ad-GFP virus infection (FIG. 27). Moreover, post-treatment of Compound I-1 or Compound II-1 after 2 hours of Ad-GFP virus infection significant decreased the number of GFP cells with a dose-dependent effect (FIG. 29(c)) as well as the MFI of GFP protein (FIG. 29(d)).

Figure 30:
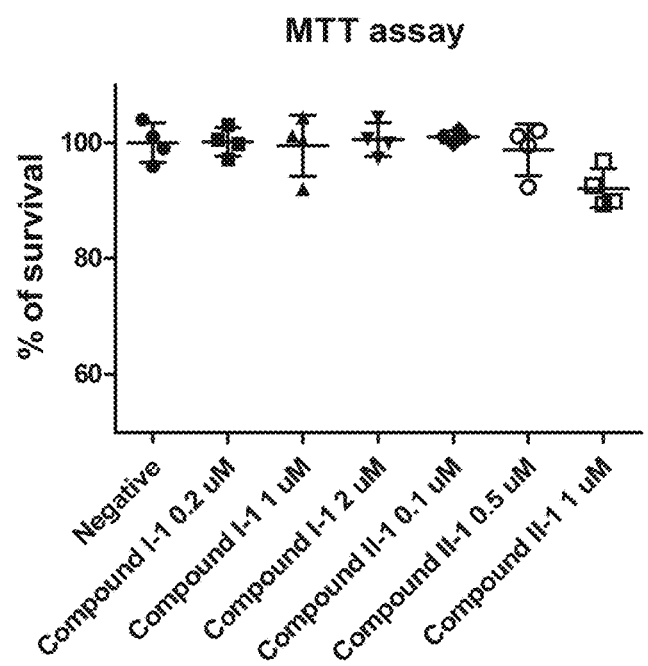
FIG. 30 illustrates the effects of the treatments of the compounds on the survival rate.

To understand whether or not inhibition of the virus infection is followed by the host cell toxicity caused by the compound treatments, we performed an MTT [3-(4,5-cimethylthiazol-2-yl)-2,5-diphenyl tetrazolium bromide] assay in cells untreated or treated with indicated compounds for 6 hours. After that, the compound is washed out and the MTT assay was tested after an additional 18 hours of fresh culture medium incubation, in a way similar to the protocol shown in FIG. 26. 0.5 mg/mL of MTT contained media was added to cells at the end of the experiment and incubated for 3 hours. Then, the supernatant was removed and the formazone crystals solubilized using 100 μl of DMSO and the absorbance at 570 nm was read using a microplate reader. The result showed a decrease of 5-10% of surviving cells in the highest dose of 1 μM Compound II-1 (FIG. 30). However, the virus inhibition effect of 50-99% is also shown at this dose of Compound II-1. Therefore, our results show that the compound effect shown by the MFI of GFP protein, which is a reporter of virus infection, was not interfered with cell density in the experiments.

Suitable dose ranges and cell toxicity levels may be assessed using standard dose range experiments that are well-known in the art. Actual dosages administered may vary depending, for example, on the nature of the disorder, e.g., stage of virus-mediated pathology, the age, weight and health of the individual, as well as other factors.

In some embodiments, the compounds in this disclosure are formulated into preparations in solid, semi-solid, liquid or gaseous forms, such as tablets, capsules, pills, powders, granules, dragees, gels, slurries, ointments, solutions, suppositories, injections, inhalants and aerosols. Administration of such formulations can be achieved in various ways, including oral, buccal, parenteral, injection, intravenous, intradermal (e.g., subcutaneous, intramuscular), topical, transdermal, transmucosal, inhalation, nasal, rectal, vaginal, etc., administration. Moreover, the compounds in this disclosure can be administered in a local rather than systemic manner, for example, in a depot or sustained release formulation.

In some embodiments, a method for treating or preventing a virus infection in a subject is disclosed. The method comprises a step of administering to the subject with the virus infection a therapeutically effective amount of a benzopyran-4-one derivative for an administration duration, i.e. the treatment duration, between 1 to 10 days to inhibit a viral replication in the subject. Some studies suggest that antiviral treatment may be beneficial in hospitalized patients when started up to 4 or 5 days after illness onset. Treatment duration might need to be altered to fit the clinical circumstances. For example, clinical judgment should be the guide regarding the need to extend treatment duration longer than 5 or 10 days for patients whose illness is prolonged. In some embodiments, the method comprises a step of identifying the subject with the virus infection. In some embodiments, the benzopyran-4-one derivative is administered intraperitoneally or subcutaneously. In some embodiments, the virus is one of an adenovirus and a retrovirus. In some embodiments, the subject is at risk of developing a viral infection. In some embodiments, the benzopyran-4-one derivative is administered at an interval selected from a group consisting of a once-daily interval, a multiple-daily interval (once every 8 or 12 hrs) and a weekly interval. Dosage adjustment may be performed to maximize efficacy and minimize toxicity. In patients with high clearance (e.g., young adults), dosing intervals shorter than 24 hrs may be more appropriate. In some embodiments, the benzopyran-4-one derivative is administered in combination with at least one agent selected from a group consisting of an antiviral agent, an antibiotic, and a steroid drug. In some embodiments, the antiviral agent is an anti-retroviral agent selected from a group consisting of a nucleoside reverse transcriptase inhibitor, a nucleotide reverse transcriptase inhibitor, a non-nucleoside reverse transcriptase inhibitor, a protease inhibitor, a fusion inhibitor, and an integrase inhibitor. In some embodiments, the virus infection is one of an adenovirus infection, which may be a respiratory infection, and a retrovirus infection.

REFERENCES

Andreassen P R, et al. ATR couples FANCD2 monoubiquitination to the DNA-damage response. Genes Dev 2004; 18(16):1958-63.

Chen H M, et al. A novel synthetic protoapigenone analogue, WYC02-9, induces DNA damage and apoptosis in DU145 prostate cancer cells through generation of reactive oxygen species. Free Radic Biol Med 2011; 50(9):1151-62.

Chen W Y, et al. Protoapigenone, a natural derivative of apigenin, induces mitogen-activated protein kinase-dependent apoptosis in human breast cancer cells associated with induction of oxidative stress and inhibition of glutathione S-transferase pi. Invest New Drugs 2011; 29(6):1347-59.

Chirnomas D, et al. Chemosensitization to cisplatin by inhibitors of the Fanconi anemia/BRCA pathway. Mol Cancer Ther 2006; 5(4):952-61.

Chiu C C, et al. Fern plant-derived protoapigenone leads to DNA damage, apoptosis, and G(2)/m arrest in lung cancer cell line H1299. DNA Cell Biol 2009; 28(10):501-6.

Lopez-Contreras A J, et al. The ATR barrier to replication-born DNA damage. DNA Repair (Amst) 2010; 9(12):1249-55.

Nghiem P, et al. ATR inhibition selectively sensitizes G1 checkpoint-deficient cells to lethal premature chromatin condensation. Proc Natl Acad Sci USA 2001; 98(16):9092-7.

Sorensen C S, et al. The cell-cycle checkpoint kinase Chk1 is required for mammalian homologous recombination repair. Nat Cell Biol 2005; 7(2):195-201.

Wang H C, et al Inhibition of ATR-dependent signaling by protoapigenone and its derivative sensitize cancer cells to interstrand cross-link-generating agents in vitro and in vivo. Mol Cancer Ther molcanther. Apr. 24, 2012; 1443

What is claimed is:

1. A method for treating or preventing a virus infection in a subject, comprising a step of:

administering to the subject with the virus infection a therapeutically effective amount of a benzopyran-4-one derivative for an administration duration between 1 to 10 days to inhibit a viral replication in the subject, wherein the benzopyran-4-one derivative is represented by formula I:

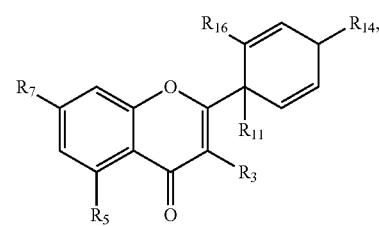

wherein each of $R_3$, $R_5$, $R_7$, $R_{11}$, $R_{14}$ and $R_{16}$ is one selected from a group consisting of a hydrogen, a hydroxyl group, a methoxyl group and an oxygen atom containing a double bond;

wherein the subject is a mammal subject, and the virus infection is one of-an adenovirus infection and a retrovirus infection; and wherein the therapeutically effective amount is an effective blood concentration of the benzopyran-4-one derivative of the subject in a range from 0.01 μM to 2 μM.

2. The method as claimed in claim 1, wherein the mammal subject includes primates, carnivore, rodent, lagomorpha, perissodactyla and artiodactyla.

3. The method as claimed in claim 1, wherein the primates includes human, ape and monkey, the carnivore includes cat and dog, the rodent includes mouse and rat, the lagomorpha includes rabbit, the perissodactyla includes horse, and the artiodactyla includes suidae, bovine and sheep.

4. The method as claimed in claim 1, wherein the adenovirus infection is a respiratory infection.

5. The method as claimed in claim 1, wherein the benzopyran-4-one derivative is administered in combination with at least one agent selected from a group consisting of an antiviral agent, an antibiotic, and a steroid drug.

6. The method as claimed in claim 5, wherein the antiviral agent is an anti-retroviral agent.

7. The method as claimed in claim 6, wherein the anti-retroviral agent is selected from a group consisting of a nucleoside reverse transcriptase inhibitor, a nucleotide reverse transcriptase inhibitor, a non-nucleoside reverse transcriptase inhibitor, a protease inhibitor, a fusion inhibitor, and an integrase inhibitor.

8. The method as claimed in claim 1, wherein the subject is administered at an interval selected from a group consisting of a once-daily interval, a multiple-daily interval and a weekly interval.

9. A method for inhibiting replication of a virus in a subject, comprising a step of:

administering to the subject at risk of developing a viral infection a therapeutically effective amount of a benzopyran-4-one derivative at an interval selected from a group consisting of a once-daily interval, a multiple-daily interval and a weekly interval, wherein the benzopyran-4-one derivative is represented by formula I:

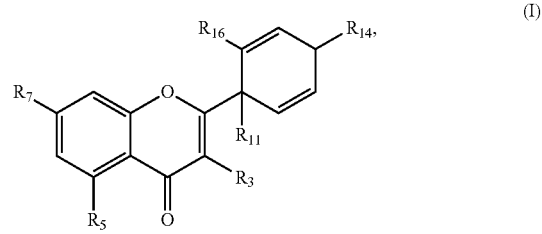

(I)

wherein each of $R_3$, $R_5$, $R_7$, $R_{11}$, $R_{14}$ and $R_{16}$ is one selected from a group consisting of a hydrogen, a hydroxyl group, a methoxyl group and an oxygen atom containing a double bond;

wherein the subject is a mammal subject, and the virus infection is one of-an adenovirus infection and a retrovirus infection; and wherein the therapeutically effective amount is an effective blood concentration of the benzopyran-4-one derivative of the subject in a range from 0.01 μM to 2 μM.

10. The method as claimed in claim 9, wherein the mammal subject includes primates, carnivore, rodent, lagomorpha, perissodactyla and artiodactyla.

11. The method as claimed in claim 10, wherein the primates includes human, ape and monkey, the carnivore includes cat and dog, the rodent includes mouse and rat, the lagomorpha includes rabbit, the perissodactyla includes horse, and the artiodactyla includes suidae, bovine and sheep.

12. The method as claimed in claim 9, wherein the retrovirus is a human immunodeficiency deficiency virus (HIV).

13. The method as claimed in claim 9, wherein the benzopyran-4-one derivative is administered intraperitoneally.

14. The method as claimed in claim 9, wherein the benzopyran-4-one derivative is administered subcutaneously.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Human ATM specific siRNA sequence

<400> SEQUENCE: 1
aagcgcctga ttcgagatcc t                                              21

<210> SEQ ID NO 2
<211> LENGTH: 21
<212> TYPE: DNA
```

```
<213> ORGANISM: Homo sapiens
<220> FEATURE:
<221> NAME/KEY: misc_feature
<222> LOCATION: (1)..(21)
<223> OTHER INFORMATION: Human ATR specific siRNA sequence

<400> SEQUENCE: 2
cctccgtgat gttgcttgat t                                              21

<210> SEQ ID NO 3
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Human DNA-PKcs specific siRNA sequence

<400> SEQUENCE: 3
gatcgcacct tactctgttg a                                              21

<210> SEQ ID NO 4
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Random siRNA sequence

<400> SEQUENCE: 4
aagtcaatat gcgactgatg g                                              21

<210> SEQ ID NO 5
<211> LENGTH: 19
<212> TYPE: DNA
<213> ORGANISM: Artificial Sequence
<220> FEATURE:
<223> OTHER INFORMATION: Synthetic construct, primer to amplyfy cDNA of
      GFP

<400> SEQUENCE: 5
caccatggtg agcaagggc                                                 19

<210> SEQ ID NO 6
<211> LENGTH: 21
<212> TYPE: DNA
<213> ORGANISM: Artificial Sequence
<220> FEATURE:
<223> OTHER INFORMATION: Syntheic construct, primer to amplify cDNA of
      GFP

<400> SEQUENCE: 6
tacttgtaca gctcgtccat g                                              21
```